United States Patent
Rosenthal

(10) Patent No.: US 7,997,280 B2
(45) Date of Patent: Aug. 16, 2011

(54) PORTABLE VAPORIZER

(76) Inventor: Joshua Rosenthal, Sherman Oaks, CA (US)

( * ) Notice: Subject to any disclaimer, the term of this patent is extended or adjusted under 35 U.S.C. 154(b) by 756 days.

(21) Appl. No.: 11/866,224

(22) Filed: Oct. 2, 2007

(65) Prior Publication Data

US 2008/0023003 A1    Jan. 31, 2008

Related U.S. Application Data

(63) Continuation-in-part of application No. 10/767,303, filed on Jan. 30, 2004, now abandoned.

(51) Int. Cl.
- *A24F 1/28* (2006.01)
- *A24F 1/22* (2006.01)
- *A24F 1/32* (2006.01)
- *A24F 13/04* (2006.01)
- *A24F 1/10* (2006.01)
- *A61M 16/00* (2006.01)
- *A61M 9/00* (2006.01)

(52) U.S. Cl. ..... 131/191; 131/194; 131/330; 128/202.21

(58) Field of Classification Search ................ 422/305, 422/306; 131/330, 173, 195, 178, 191, 194, 131/329, 305; D27/162, 169; 206/242, 244, 206/259; 128/202.21

See application file for complete search history.

(56) References Cited

U.S. PATENT DOCUMENTS

| | | | |
|---|---|---|---|
| 239,196 A * | 3/1881 | Rousseaux | 128/202.21 |
| 87,603 A | 3/1889 | Tichenor | |
| 437,070 A | 9/1890 | Wiesebrock | |
| 649,521 A | 5/1900 | Libbey | |
| 1,071,389 A | 8/1913 | Blosser | |
| 1,405,802 A | 2/1922 | Phelan | |
| 2,104,266 A | 1/1938 | McCormick | |
| 4,031,904 A * | 6/1977 | Karl | 131/173 |
| 4,036,240 A * | 7/1977 | Murray, Jr. | 131/173 |
| 4,141,369 A | 2/1979 | Burruss | |
| 4,187,885 A * | 2/1980 | Kahler | 138/89 |
| 4,219,032 A | 8/1980 | Tabatznick | |
| 4,233,998 A * | 11/1980 | Radey, Jr. | 131/175 |
| 4,303,083 A | 12/1981 | Burruss | |
| 4,340,072 A | 7/1982 | Bolt | |
| 4,474,191 A | 10/1984 | Steiner | |
| 4,735,217 A | 4/1988 | Gerth | |
| 4,907,606 A | 3/1990 | Lilja | |
| 4,922,901 A | 5/1990 | Brooks | |
| 4,947,874 A | 8/1990 | Brooks | |
| 4,947,875 A | 8/1990 | Brooks | |
| 5,042,509 A | 8/1991 | Banerjee | |
| 5,060,671 A | 10/1991 | Counts | |
| 5,099,861 A | 3/1992 | Clearman | |
| 5,105,831 A | 4/1992 | Banerjee | |

(Continued)

OTHER PUBLICATIONS

CheapVaporizer.com; <http://www.cheapvaporizer.com/main.html>; Jan. 2, 2003.

(Continued)

*Primary Examiner* — Sean Conley
*Assistant Examiner* — Regina Yoo
(74) *Attorney, Agent, or Firm* — George P. White; Mark E. Hankin

(57) ABSTRACT

The present invention relates to a hand-operated and portable vaporizing device that, through the application of heat, successfully volatilizes one or more constituents of various vaporizable substances, such as medicines, cigarettes, and plant materials, for the purpose of inhaling these volatilized constituents.

10 Claims, 13 Drawing Sheets

U.S. PATENT DOCUMENTS

| | | | |
|---|---|---|---|
| 5,156,170 A | | 10/1992 | Clearman |
| 5,224,498 A | | 7/1993 | Deevi et al. |
| 5,249,586 A | | 10/1993 | Morgan |
| 5,345,951 A | | 9/1994 | Serrano |
| 5,388,574 A | | 2/1995 | Ingebrethsen |
| 5,388,594 A | | 2/1995 | Counts |
| 5,402,803 A | * | 4/1995 | Takagi ............... 131/200 |
| 5,564,442 A | | 10/1996 | MacDonald |
| 5,819,756 A | | 10/1998 | Mielordt |
| 5,993,748 A | | 11/1999 | Wheeler |
| 6,026,820 A | * | 2/2000 | Baggett et al. ............. 131/373 |
| 6,095,153 A | | 8/2000 | Kessler |
| 6,148,826 A | * | 11/2000 | Lancaster et al. ............. 131/191 |
| 6,250,301 B1 | | 6/2001 | Pate |
| 6,354,301 B2 | | 3/2002 | McCoy |
| 6,481,437 B1 | | 11/2002 | Pate |
| 6,513,524 B1 | | 2/2003 | Storz |
| 6,532,965 B1 | | 3/2003 | Abhulimen |
| 6,598,607 B2 | | 7/2003 | Adiga |
| 7,415,982 B1 | * | 8/2008 | Sheridan ............... 131/191 |
| 2002/0069886 A1 | | 6/2002 | Couch |
| 2002/0074006 A1 | | 6/2002 | Gunn |
| 2002/0162969 A1 | | 11/2002 | Reed |

OTHER PUBLICATIONS

The VaporTech Vaporizer; <http://www.vaportechco.com/view.html>; Jan. 2, 2003.

GrassCity.com; <http://shop.grsscity.com/cgi-bin/grasscity/1050.html>; Jan. 3, 2003.

The "VaporTechniques" Vaping Methods; <http://www.vaportechco.com/meth.html>; Jul. 23, 2007.

Vaporizer Giant; <http://www.vaporizergiant.com/cheap-vaporizer.html>; Jul. 23, 2007.

MarijuanaVaporizer.com; <http://marijuanavaporizer.com/vaporizer_review/cheap-vaporizer.html>; Jul. 23, 2007.

Herbal Vaporizer from Cannabis Heaven; <http://cannabisheaven.co.uk/vaporizers/the-bubble-vap.htm>; Aug. 6, 2007.

* cited by examiner

PORTABLE VAPORIZER

RELATED APPLICATIONS

This application is a continuation-in-part of U.S. application Ser. No. 10/767,303 entitled "Portable Vaporizer," invented by Joshua Rosenthal and filed Jan. 30, 2004, now abandoned; the contents of which are incorporated by reference in their entirety.

FIELD OF INVENTION

This invention relates, generally, to heat vaporizers for producing inhalable vapors; more particularly to heat vaporizers that are compact, portable, and can be easily and conveniently hand-operated and hand-carried.

BACKGROUND

Vaporization of volatile constituents of various substances without combustion by the application of heat for the purpose of inhaling said volatile constituents is a process that has been known for quite some time. U.S. Pat. No. 87,603 of Mar. 9, 1869 discloses the construction of a vaporizer that makes use of heated stones, heated metal or coals in an isolated chamber and the conduction of heat therefrom to release volatile constituents from medicinal substances in an adjacent chamber in order to make possible inhalation of said volatile constituents.

Since that time, numerous vaporizing devices of varied design and various levels of sophistication have been disclosed. Some use heat from electrical heating elements as a means to accomplish vaporization without combustion, such as those disclosed in U.S. Pat. Nos. 2,104,266; 4,141,369; 4,303,083; 4,735,217; 4,907,606; 4,922,901; 4,947,874; 4,947,875; 5,060,671; 5,224,498; 5,249,586; 5,388,574; 5,388,594; 5,819,756; and 6,095,153. Other devices use the application of heat from a flame through an intermediary barrier of glass, metal, or other heat conducting material, thereby preventing direct contact of the flame with the substance to be vaporized, such as those disclosed in U.S. Pat. Nos. 437,070; 649,521; 1,071,389; and 1,405,802. Still other devices rely on the transfer of heat from the combustion of a solid fuel source, generally a carbonaceous material, such as those disclosed in U.S. Pat. Nos. 4,219,032; 4,340,072; 4,474,191; 5,042,509; 5,099,861; 5,105,831; 5,156,170; 5,345,951; and 6,598,607 (liquid fuel). And then there are a number of devices that rely on the application of internally or externally produced hot air to a vaporizable substance in order to achieve vaporization such as those disclosed in U.S. Pat. Nos. 5,993,748; 6,250,301; 6,481,437; 6,354,301; 6,513,524; and 6,532,965 (steam).

As outlined, for example, in U.S. Pat. Nos. 4,141,369; 4,303,083; 5,993,748; and 6,481,437; an advantage of vaporization of a vaporizable substance over standard combustion of that same substance is the elimination of unwanted combustion byproducts and therefore a reduction in the health risks associated with inhalation of said combustion byproducts. Some devices, however, such as those disclosed in U.S. Pat. Nos. 4,219,032; or 4,340,072, actually make direct use of the hot combustion gases from the fuel source for heating the vaporizable substance and therefore fail to effectively release various volatile constituents from substances while avoiding the commingling of said volatile constituents with unwanted combustion by-products.

Depending upon the particular substance to be vaporized, vaporization also has other advantages over standard combustion, such as more efficient use (i.e., less waste) of the vaporizable substance, elimination of production and release of unwanted smoke fumes into the ambient atmosphere, improved taste, etc.

Although they may effectively vaporize vaporizable substances, many of the devices referred to above also have disadvantages:

All those devices utilizing resistive electrical heating elements as heating means will necessarily require a cumbersome or non-portable source of electricity so they must either be plugged into an electrical outlet or be attached to a battery large enough to generate sufficient heat to bring about vaporization and that can accomplish its function long enough so as to not to require constant replacement.

Those devices mentioned above that utilize an enclosed or built-in flame as a heat source are too cumbersome to easily be carried in a pocket or purse. And the device disclosed in U.S. Pat. No. 1,405,802, would most likely require 3 hands to operate properly if one attempted to use a hand-held lighter as the heat source rather than a self-supported standing burner as heat source.

Those devices that make use of solid fuel 1) require the purchase and supply of solid fuel rods, disks, etc. 2) release combustion products into the ambient atmosphere that may be offensive and/or hazardous to others in the vicinity as well as to the user of the device. In addition these devices pose fire hazards similar to burning cigarettes when not properly attended.

Further disadvantages include:

1) Many of the devices mentioned in all categories are expensive to produce.

2) Some of the devices hold the vaporizable substance in compartments that are hidden from view, making visual inspection and assessment of the state of the vaporizable substance more difficult once the vaporization process has begun.

3) Some devices require a continual supply of replacement parts, specialized fuel modules, or specially prepared vaporizable substances.

In addition to patented devices, there are also a number of other devices that have been disclosed in periodicals or are on the open market. In examining the various devices available, it is evident that they suffer from drawbacks similar to those outlined above. Many of these devices are quite expensive and cumbersome while the less expensive, more portable models are not completely effective at isolating combustion byproducts from desired volatile substances. In addition, some of the existing models of vaporizer require that the vaporizer, once 'loaded' with vaporizable substance, must be held relatively still in order to prevent the vaporizable substance from moving out of proper vaporizing position, and are thus unsuitable for transport once 'loaded' or for use in relatively unstable physical environments (e.g., during a bumpy car-ride).

One example of a known vaporizing device is the "ubie vaporizer" or "cheap vaporizer," which includes a mouthpiece tube insertable within an outer vaporizer tube. The distal ends of the tubes include venting holes to establish a direct airflow path in a straight line from the atmosphere to the mouthpiece. The outer vaporizer tube is configured to receive the substance, such that the substance is in direct contact with the heated outer vaporizer tube. Accordingly, the "cheap vaporizer" heats the substance directly via conduction caused by contact with the outer vaporizer tube, resulting in lack of control. The "cheap vaporizer" additionally lacks any ability to stabilize the substance, or to humidify the substance. Furthermore, because the outer vaporizer tube is heated during use, the "cheap vaporizer" creates the danger of burns or other heat-related hazards.

Another example of a known vaporizing device is the "smoke-bubble," consisting of an outer bubble-shaped vessel for receiving the substance, fitted with a stopper having an inlet vent and a mouthpiece tube extending into the outer vessel. Due to the shape of the outer vessel, only negligible amounts of heat are transmitted to the mouthpiece tube that is spaced far away from the outer wall. Accordingly, the "smoke-bubble" device is limited in that the substance must be placed in direct contact with the outer vessel in order to be heated, involving similar heating difficulties and dangers as set forth above.

It therefore would be desirable to provide a vaporizer: 1) that effectively separates desired volatile substances from unwanted combustion byproducts, 2) that is inexpensive to manufacture, 3) that is of such size and weight as to be easily hand-operated and portable, 4) that can operate successfully using an external or compact and portable internal heat source, 5) that regularly requires no other specialized replacement supplies such as specialized fuel rods, disks, mixtures, etc. besides the vaporizable substance itself, 6) in which the vaporizable substance can be substantially contained in the vaporization chamber once inserted and can substantially remain in proper vaporizing position even if the 'loaded' vaporizer is turned in space, shaken, carried in the pocket or purse, etc., 7) that allows enjoyment of the full flavor of the vaporizable constituents without metallic, combustion, or other unwanted taste, 8) in which vaporization can easily be controlled with pinpoint accuracy, and started and stopped quickly so as to avoid substantial waste of the vaporizable substance, and 9) that is preferably transparent, allowing easy visual assessment of the physical state of the vaporizable substance at any point during the vaporization process.

SUMMARY OF THE INVENTION

The present invention relates to a device for vaporizing volatile constituents of a substance. The device includes an elongate outer vessel having an inner surface, an outer surface, a proximal end and a closed distal end. The closed distal end is formed by a heating body comprising a material that can withstand heat required to vaporize said volatile constituents. The proximal end is formed by a venting body. The device also includes an elongate inner vessel having an inner passage dimensioned to receive the substance, an outer surface and open distal and proximal ends and being insertable into said elongate outer vessel and extending within the heating body and the venting body so as to leave a space between adjacent walls of said elongate inner vessel and said heating and venting bodies, and a space between the inner vessel open distal end and the outer vessel closed distal end. The device further includes one or more body vents located on the venting body away from the heating body for admitting atmospheric air along an airflow pathway. The airflow pathway is formed by the space between the inner surface of the elongate outer vessel and the outer surface of the elongate inner vessel, the space between the distal ends of the elongate inner and outer vessels, the inner passage, and the proximal end of the elongate inner vessel.

The present invention also relates to a device for vaporizing volatile constituents of a substance, the device including an elongate heating body comprised of a material for withstanding the application of vaporizing heat and having an inner surface, a closed distal end and an open proximal end. The device includes an elongate venting body having an inner surface and an open distal end. The venting body open distal end is fastened to the heating body open proximal end, thereby forming an elongate outer vessel. The device also includes an elongate inner vessel having an inner passage dimensioned to receive the substance, an outer surface, an open proximal end, and an open distal end, the inner vessel being positioned within the venting body and the heating body such that the outer surface of the inner vessel is spaced from and adjacent to the inner surface of the heating body and the inner surface of the venting body. The inner vessel open distal end is spaced from the heating body closed distal end, such that the open proximal end of the inner vessel is in fluid communication with the inner passage and the space between the inner vessel and the outer vessel via the open distal end of the inner vessel. The device yet further includes a retainer insertable into the inner vessel distal end to retain the substance within the inner vessel and heating body. The venting body includes one or more air intake vents located away from the heating body establishing fluid communication with surrounding air and the space between the inner vessel and the outer vessel.

The present invention further relates to a device for vaporizing volatile constituents of a substance, the device including an elongate outer vessel having a closed distal end formed by a heating body and a proximal end formed by a venting body; an elongate inner vessel having an inner passage dimensioned to receive the substance and being insertable into said elongate outer vessel and extending within the heating body and the venting body so as to leave a space between adjacent walls of said elongate inner vessel and said elongate outer vessel; and one or more body vents located on the venting body away from the heating body.

The present invention yet further relates to a device for vaporizing volatile constituents of a substance, the device including: an elongate outer vessel having a closed distal end formed by a heating body and a proximal end formed by a venting body; an elongate inner vessel having an inner passage dimensioned to receive the substance and being insertable into said elongate outer vessel and extending within the heating body and the venting body so as to leave a space between adjacent walls of said elongate inner vessel and said elongate outer vessel; and one or more body vents located on the venting body away from the heating body; wherein: the outer vessel further comprises a stabilizer extending inward from elongate outer vessel to position the elongate inner vessel within the elongate outer vessel and maintain spacing between the elongate inner and outer vessels; and the device further comprises a retainer structured to retain the substance within the inner vessel.

The present invention yet further relates to a portable vaporizing kit, comprising: a portable device for vaporizing volatile constituents of a substance, the device comprising an elongate outer vessel having a closed distal end formed by a heating body and a proximal end formed by a venting body; an elongate inner vessel having an inner passage dimensioned to receive the substance and being insertable into said elongate outer vessel and extending within the heating body and the venting body so as to leave a space between adjacent walls of said elongate inner vessel and said elongate outer vessel; one or more body vents located on the venting body away from the heating body; and a permeable sock enclosing a proximal end of the elongate inner vessel; a portable moisturizing pipette; and a portable storage case structured to secure the portable device and portable moisturizing pipette.

Other features and advantages of this invention will become apparent from the following description of several embodiments of the invention, taken in conjunction with the accompanying drawings, which illustrate, by way of example, the principles of the invention.

DETAILED DESCRIPTION OF THE DRAWINGS

In the following detailed description of various embodiments of the invention, numerous specific details are set forth in order to provide a thorough understanding of various aspects of one or more embodiments of the invention. However, one or more embodiments of the invention may be practiced without these specific details. In other instances, well-known methods, procedures, and/or components have not been described in detail so as not to unnecessarily obscure aspects of embodiments of the invention.

Figure 1:
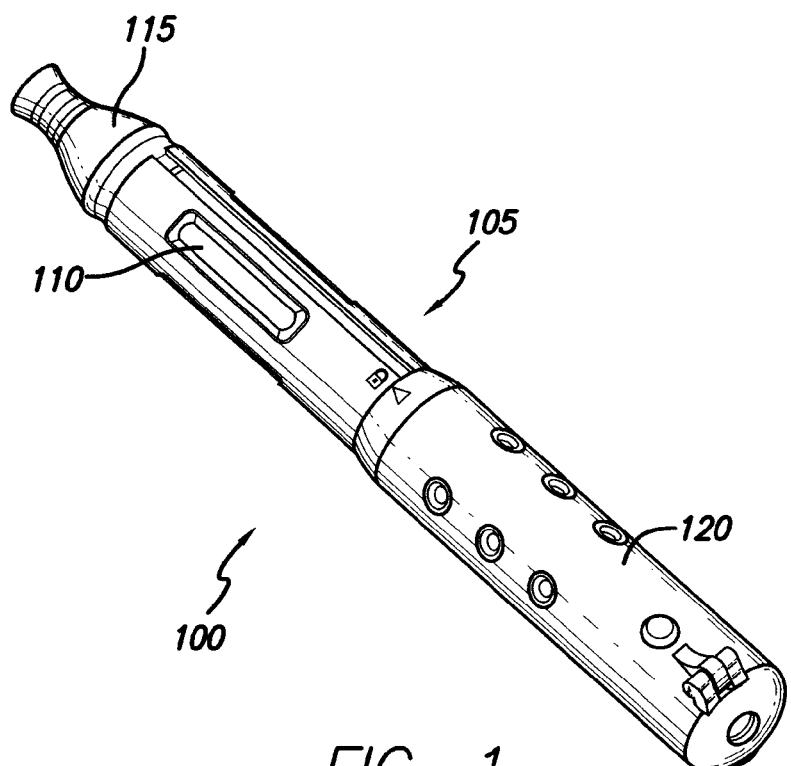
FIG. 1 is a perspective view of an embodiment of the present invention.

FIG. 1 illustrates an embodiment of a portable vaporizer 100 according to the present invention. The portable vaporizer 100 includes an elongate outer vessel 105, and an elongate inner vessel 110 disposed within the elongate outer vessel 105. The portable vaporizer 100 is illustrated with a mouthpiece 115 and elongate shield 120.

Figure 2:
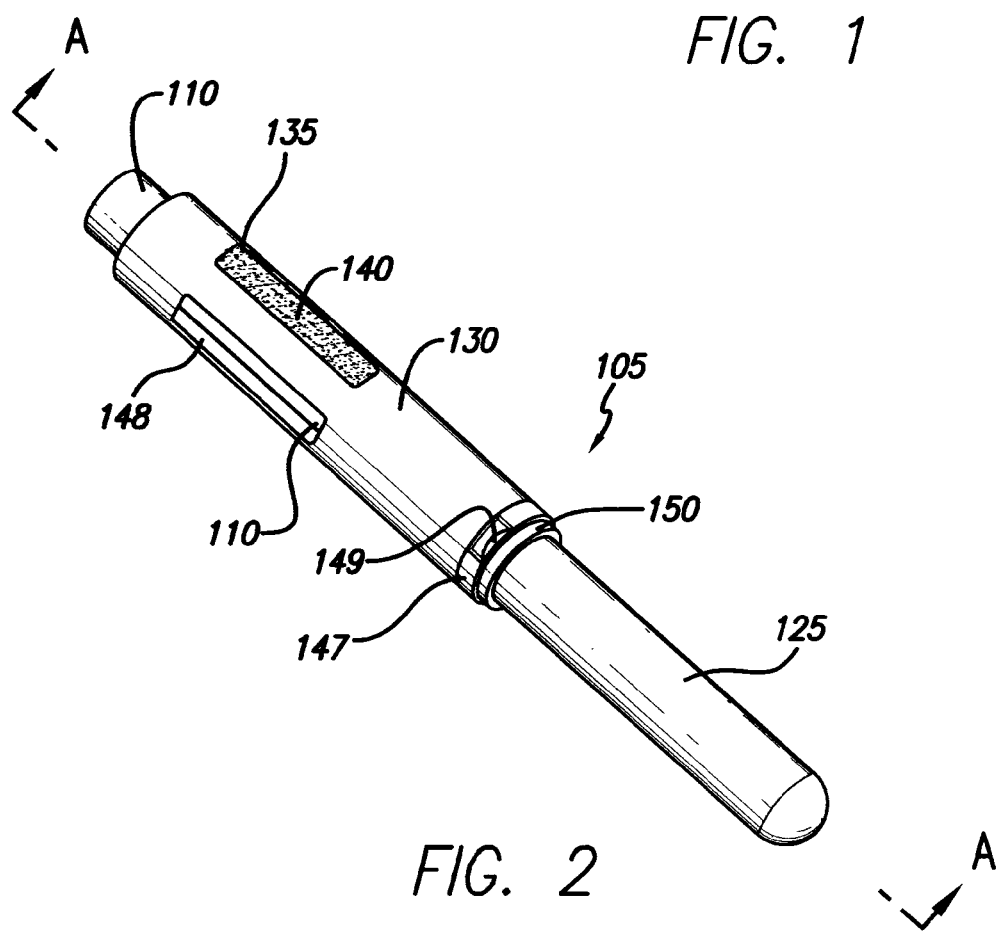
FIG. 2 is a perspective view of an embodiment of the present invention.

FIG. 2 illustrates the elongate outer vessel 105 in greater detail, with the mouthpiece 115 and elongate shield 120 removed so as to reveal the underlying components. The distal end of the elongate outer vessel 105 is formed by a heating body 125. The proximal end of the elongate outer vessel 105 is formed by a venting body 130 attached to the heating body 125. The venting body 130 includes one or more body vents 135. An elongate inner vessel 110 extends within the venting body 130 and the heating body 125.

The number of body vents 135, their exact size and their exact placement can be varied. However, arranging the body vents 135 away from the heating body 125 provides separation between the air flowing into the portable vaporizer, and the air in the vicinity of heat application at the heating body 125. Thus, the structure of the portable vaporizer 100 creates an airflow pathway that minimizes the intake of heating fuel exhaust fumes into the portable vaporizer 100 and into the user's lungs. The body vents 135 are preferably arranged on the venting body 130 such that it is difficult for a user to obstruct all of the body vents 135 to the extent that airflow is substantially hindered through the portable vaporizer 100.

Figure 3:
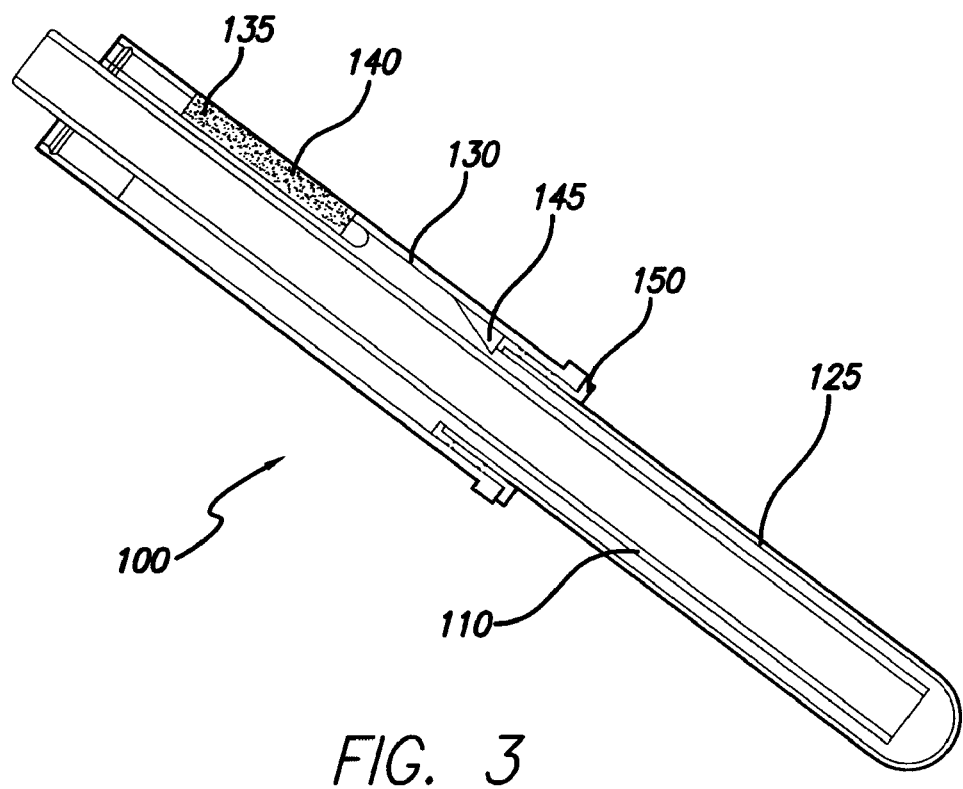
FIG. 3 is a longitudinal cross-sectional view of the embodiment illustrated in FIG. 2 along line A-A.

FIG. 3 illustrates the elongate inner vessel 110 of the portable vaporizer 100 extending within the venting body 130 and the heating body 125. The venting body 130 includes stabilizer 145, which extends inward from the venting body 130 to position the elongate inner vessel 110 within the venting body 130 and the heating body 125. The venting body 130 also includes body vents 135 for admitting air into the venting body 130 along an airflow pathway. A heating body fastener 150 fastens the venting body 130 to the heating body 125.

The venting body 130 is preferably constructed from a lightweight material having sufficient strength, rigidity, and durability. An exemplary material is ABS plastic. Additionally, the venting body 130 can be constructed with a flame retardant additive to avoid catching fire.

As illustrated in FIG. 2, the venting body 130 can include venting body cut-outs 149 at the distal end of the venting body 130. The venting body cut-outs 149 are crescent-shaped and expose a portion of the underlying heating body fastener 150. Accordingly, the venting body cut-outs 149 facilitate disassembly of the elongate outer vessel 105 by providing a gripping portion to remove the heating body fastener 150 from the venting body 130. Accordingly, the user can remove the heating body fastener 150 from the venting body 130 without needing to grip the heating body 125. Such a feature is beneficial to enable to user to more safely remove a heating body 125 that has been broken, via the gripping portions of the heating body fastener 150 exposed via the venting body cut-outs 149.

The venting body 130 can also include raised body ring 147. The raised body ring 147 is arranged to extend in a radial direction from the venting body 130, to provide a surface for the elongate shield 120 to ride upon. The raised body ring 147 can include a discontinuity spacing corresponding to the venting body cut-outs 149. The discontinuity enables the user to slide a finger or tool along the venting body 130 to grip the heating body fastener 150 via the venting body cut-outs 149, without catching the finger or tool on the raised body ring 147. The venting body can also include grips for gripping the portable vaporizer 100.

The airflow pathway is established in part by the cooperation of the venting body 130, the heating body 125, and the elongate inner vessel 110. A proximal end of the elongate inner vessel 110 protrudes out through the proximal end of the venting body 130, thus making the proximal end of the elongate inner vessel 110 available for inhalation therethrough. When air is inhaled out through the proximal end of the elongate inner vessel 110, a suction is created that draws air along the airflow pathway, in through body vents 135, distally between the inner surface of the heating body 125 and the outer surface of the elongate inner vessel 110, then into the elongate inner vessel 110, and out through the open proximal end of the elongate inner vessel 110.

Body vents 135 can be formed by openings of various design through the venting body 130. The body vents 135 can be placed in any number of patterns, using a smaller or larger number of body vents 135, as well as a somewhat smaller or larger vent size, or even different shaped body vents 135. The number and size of the body vents 135 chosen can also affect the drawing pressure necessary to produce a given airflow through the portable vaporizer 100.

The body vents 135 can include body vent filters 140, through which the airflow pathway passes. For example, the body vent filters 140 can be activated carbon elements, to remove particulates, odors, and other contaminants from the airflow. Additionally, body vents 135 can include louvers 148 (FIG. 2), which are operable to selectively block the airflow through body vents 135. The louvers 148 can be manually rotatable or slidable via a knob or lever. The louvers 148 can also be activated according to a spring or coil, including a heat-activated bimetal element that adjusts the position of the louvers 148 according to the temperature of the airflow and/or the venting body 130 and/or the elongate inner vessel 110.

When a vaporizable substance is disposed into the distal end of the elongate inner vessel 110, and heat from a heat source is applied to the heating body 125 while air is suctioned through the portable vaporizer 100, air passing within the heating body 125 and onward into the elongate inner vessel 110 is heated by convection and radiation, by heat radiating from and penetrating through the heating body 125. This heated air subsequently heats the vaporizable substance disposed at the distal end of the elongate inner vessel 110, causing vaporization of various volatile constituents of the vaporizable substance. The heated air then carries the volatilized constituents with it out through the opening in the proximal end of the elongate inner vessel 110.

For most embodiments it is preferable that in assembled position, all parts of the heating body fastener 150 be located away from the distal end of the heating body 125 so as to avoid heating the heating body fastener 150 and/or interfering with the heating of the heating body 125. A grommet, made preferably of rubber or other elastic material, has been chosen as a non-limiting example of a heating body fastener 150 for a number of reasons, including that it is effective, easy to use, inexpensive, unobtrusive, and easily replaceable.

A number of materials can be employed for construction of the heating body 125 and elongate inner vessel 110 of the present embodiment, including glass, metal, and ceramic, as well as combinations of material such as metal bonded to glass, etc. High temperature glass, such as borosilicate or PYREX®, has the advantages of being durable, inexpensive, transparent, and non-reactive to prevent negative affects on the quality and taste of the vapors produced. This type of material is also appropriately but not excessively conductive of heat, as heat conducted along the heating body 125 remains substantially confined to the distal end of the device when the heating body 125 is made of this material, making the portable vaporizer 100 easier and safer to handle during and after usage. Furthermore, high temperature glass enables direct heat transfer through the heating body 125 and/or the elongate inner vessel 110 via radiation, enabling pinpoint heating of specific locations of the substance within the elongate inner vessel 110. The heating body 125 can be formed by a standard test tube shape, having an open proximal end and a rounded closed distal end.

The elongate inner vessel 110 may be made of a high temperature glass in the shape of a tube, straight throughout most of its length, with an open proximal end and an open distal end.

The portable vaporizer 100 can include electronics for temperature sensing, moisture sensing, and/or illumination. For example, the heating body 125 and/or the elongate inner vessel 110 can be illuminated via light sources (e.g., LED lamps) to provide the user with enhanced visual illumination and feedback of the vaporization status of the substance. Additionally, the lighting can be color-coordinated to communicate operational status of the portable vaporizer 100. For example, the portable vaporizer 100 can include temperature sensors, which are configured to modify the color of the lighting to visually communicate the temperatures of the various parts of the portable vaporizer 100. Because different substances require varying temperatures for optimal vaporization, the sensors and/or light sources can include settings corresponding to a range of substances, such that the status corresponds to the temperature of the substance. Visual feedback can be provided by illuminating the glass portions of the portable vaporizer such that the light is communicated throughout the glass surfaces. Visual feedback can also be provided directly in the form of status LEDs arranged on the surface of the portable vaporizer 100, along with corresponding explanatory indicia which explains the status LEDs. Accordingly, the electronics can communicate when the portable vaporizer 100 has achieved an appropriate temperature and/or humidity level for optimal vaporization, corresponding to specific vaporizable substances.

Figure 4:
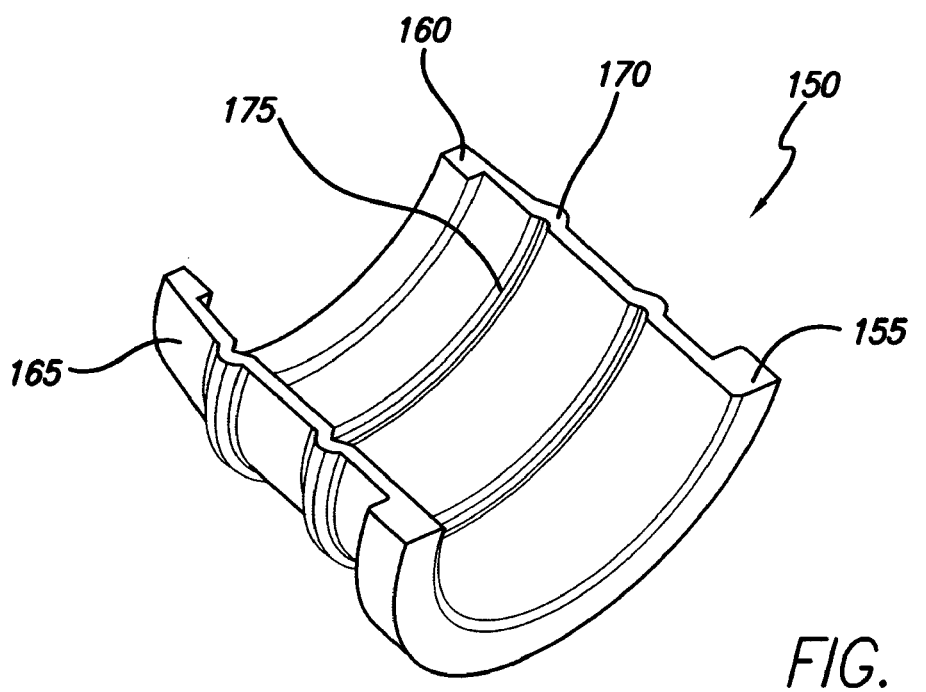
FIG. 4 is a perspective view of a cross-section of the fastener illustrated in FIG. 3, the cross-section of the fastener removed from the portable vaporizer.

FIG. 4 illustrates a cross-sectional view of an embodiment of heating body fastener 150. The illustrated embodiment is structured to act as a seal between the larger inner diameter of the venting body 130, and the smaller outer diameter of the heating body 125, when the bodies are arranged to share a coaxial overlap coextensive with the heating body fastener 150. Such an arrangement is illustrated in FIG. 3. The illustrated heating body fastener 150 includes an outer flange 155, structured to abut the distal end of the venting body 130. The heating body fastener 150 also includes an inner flange 160, structured to abut the proximal end of the heating body 125. Accordingly, the fastener arranges the venting body 130 in coaxial relation with the heating body 125. The heating body fastener 150 can also include a fastener taper 165, to facilitate insertion of the heating body fastener 150 on the distal end of the venting body 130.

The heating body fastener 150 can include a flexible ridge 170 to sealably engage the venting body 130 and the heating body 125. The flexible ridge 170 illustrated in FIG. 4 is compressible, such that it can accommodate variations in diameters between the venting body 130, the heating body 125, and the heating body fastener 150. As illustrated, the flexible ridge 170 is compressible via an air space indention 175 corresponding to the flexible ridge 170. Accordingly, the heating body fastener 150 maintains a proper seal, and protects the venting body 130 and heating body 125 from stresses and/or breakage.

Alternatively, the outer body fastener 150 can include a central flange arranged between proximal and distal ends of the outer body fastener 150, instead of outer flange 155. Accordingly, the outer body fastener 150 can sealably fasten a venting body 130 and heating body 125 having equal diameters, or unequal diameters sealably arranged such that the bodies are not overlapping coaxially.

Figure 5:
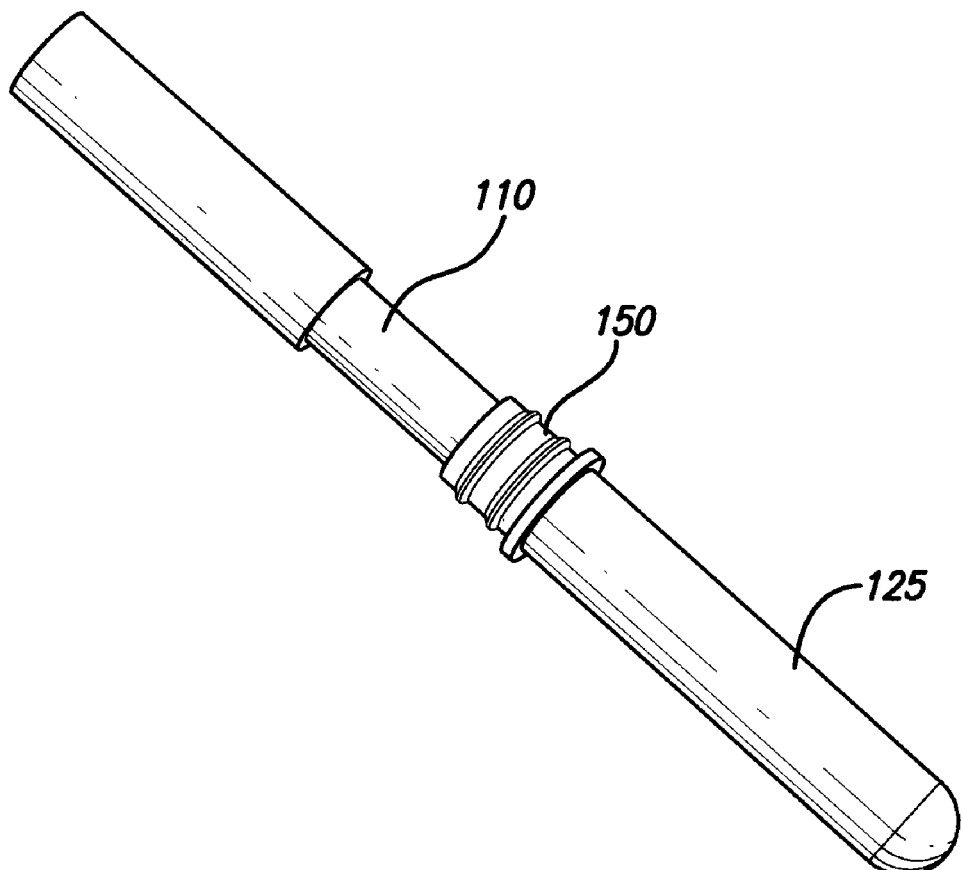
FIG. 5 is a perspective view of an embodiment of the present invention.

FIG. 5 illustrates the heating body fastener 150 attached to the heating body 125. The venting body is removed to reveal the elongate inner vessel 110. The heating body fastener 150 is preferably constructed from a flexible material, such as silicone, that can act as a heat barrier and that has a high tolerance for heat. The fastener preferably is structured such that it is easily releasable for ready disassembly and reloading of the portable vaporizer 100. Rubber or silicone materials have some distinct advantages, including the ability to grip glass well to produce a relatively strong removable locking seal in the assembled elongate outer vessel 105. Further, such materials absorb shock thereby minimizing impacts transferred to the glass. The heating body fastener 150 can be colored red or other colors to warn of the presence of heat or to warn that the heating body should never be touched with bare hands.

The heating body 125 and/or the elongate inner vessel 110 are preferably sufficiently thick to withstand applied heat, the hot air flow through the portable vaporizer 100, and the repeated surface to surface contact involved in assembling and disassembling the portable vaporizer 100. The heating body 125 and/or the elongate inner vessel 110 are also preferably sufficiently thin to allow ready heat transfer, e.g., conduction, convection, and radiation, from a heat source through the surface of the heating body 125 to the air in between the heating body 125 and the elongate inner vessel 110, and to the substance within the elongate inner vessel 110.

It is desirable that the user's hand will not be burned before, during, and after use. Preferably there is sufficient distance between the heating body 125 and the area where the hand holds the device, e.g., near the proximal end of the elongate outer body 110, so as to eliminate unacceptable levels of heat transfer to the user's hand or facial area. The characteristics and arrangement of the materials and components used for construction can be selected so as to prevent excessive heat transfer to the proximal end of the inner vessel and venting body, so that a user's lips and hands are not burned.

Figure 6:
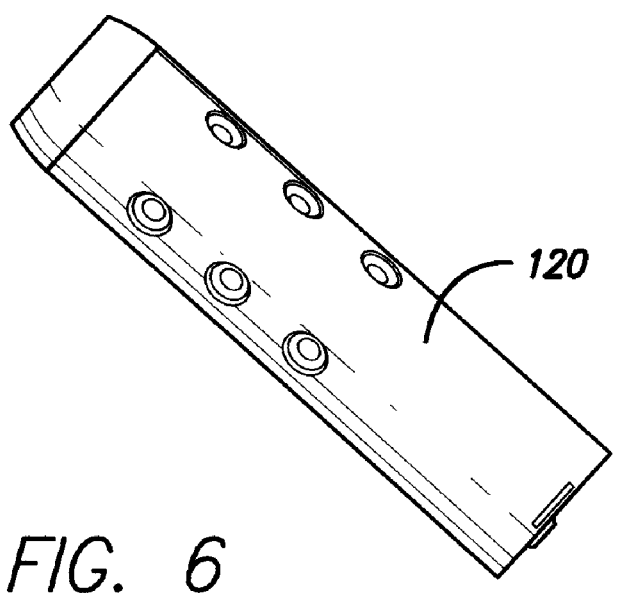
FIG. 6 is a perspective view of an elongate shield used in connection with an embodiment of the present invention.

FIG. 6 illustrates the elongate shield 120 structured to slidingly engage the elongate outer vessel 105. The elongate shield 120 can be arranged along the elongate outer vessel 105 in a distal position, for protecting the heating body 125, and a proximal position, for exposing the heating body 125.

Figure 7:
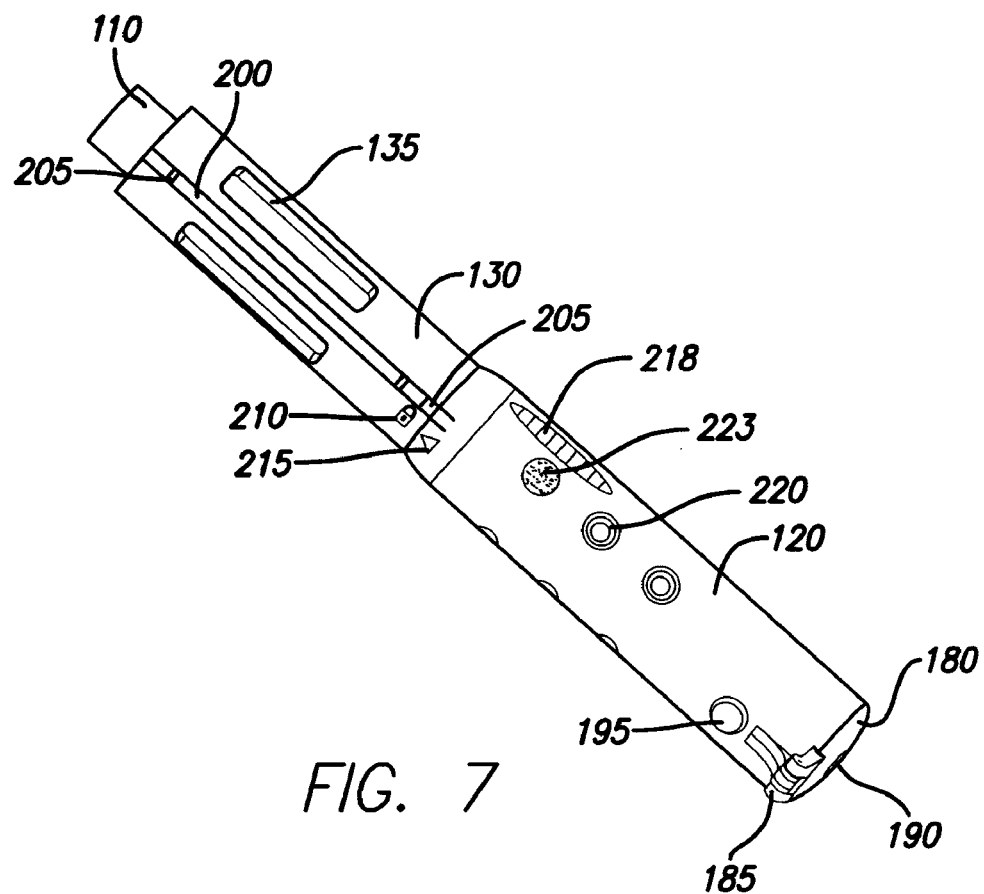
FIG. 7 is a perspective view of an embodiment of the present invention illustrating an elongate shield in a distal position.

FIG. 7 illustrates the elongate shield 120 interfacing with the venting body 130. The elongate shield 120 is in the distal position protecting the heating body (not visible in FIG. 7). The elongate shield 120 includes an end cap 180 attached to the elongate shield 120 by a hinge 185. The end cap 180 includes a cap vent 190. When the end cap 180 is in a fully open position, the cap vent 190 snaps onto the raised button 195 to maintain the end cap 180 in the open position (e.g., see FIG. 16). The hinge 185 and/or the opened end cap 180 can prevent the portable vaporizer 100 from rolling. The inner surface of the end cap 180 can include feet, such that when in an opened position, the feet are exposed to act as a stand and support for the portable vaporizer 100. The end cap 180 can include a raised finger tab, which extends outward from the end cap 180 beyond the circumference of the elongate shield 120, to provide a grip for opening and closing the end cap 180. The elongate shield 120 can include grips 218, such as in-molded rubber grips, for enhancing the user's grip.

The elongate shield 120 interacts with at least one body channel 200 in the venting body 130. Body channel 200 can include one or more channels, and can include one or more raised humps 205 that cooperate with the elongate shield 120 to provide a clicking feedback when the shield is moved into and between the distal position and the proximal position. Furthermore, the venting body 130 can include a circumferential channel to allow the elongate shield 120 to rotate into a locked position about the venting body 130. The locked position is indicated by locked indicia 210, positioned on the venting body 130 to correspond to the arrow 215 positioned on the elongate shield 120. Preferably, the force required to slide the shield into and between positions, including locked positions, is less than the force required to disassemble the portable vaporizer 100. The elongate shield 120 protects the elongate inner vessel 110 and elongate outer vessel 105 from breakage or inadvertent contact. While in the locked position, the elongate shield 120 minimizes the risk of breakage of the elongate inner vessel 110 and elongate outer vessel 105, even when the portable vaporizer 100 is dropped on its distal end. In the event that the elongate inner vessel 110 and/or the elongate outer vessel 105 suffer breakage, the elongate shield 120 encloses the broken vessels, protecting them from inadvertent contact. The elongate shield 120 can further contain portions of the broken vessels, further protecting the user from inadvertent contact with broken glass which would otherwise be ejected from the portable vaporizer 100 in the absence of the elongate shield 120.

The elongate shield 120 includes a plurality of shield vents 220, positioned along the elongate shield 120 to allow airflow to the heating body 125 when the elongate shield 120 is in the distal position. Furthermore, the shield vents 220 are arranged to correspond to the body vents 135 of the heating body 130, when the elongate shield 120 is in the proximal position exposing the heating body 130. Accordingly, the shield vents 220 can be arranged to provide the benefit of preventing inadvertent obstruction by the user, due to the spacing circumferentially about the elongate shield 120. As illustrated in FIG. 7, the elongate shield 120 has been rotated into the locked position, so the shield vents 220 are out of alignment with the body vents 135 of the venting body 130.

Preferably, the shield vents 220 are of small enough diameter to provide a safety feature by preventing finger contact of the underlying heating body 125, even by the very small fingers of a child. The shield vents 220 can include shield vent filters 223, for filtering the airflow pathway when the elongate shield 120 is in the proximal position wherein the shield vent filters 223 are positioned over the body vents 135.

Figure 8:
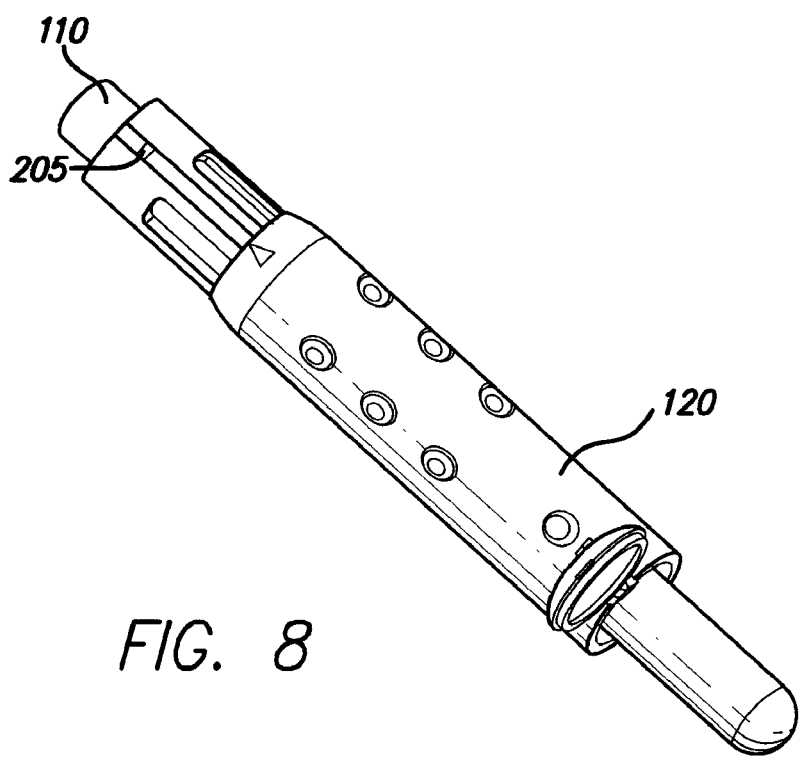
FIG. 8 is a perspective view of an embodiment of the present invention illustrating an elongate shield in an intermediate position.

FIG. 8 illustrates the elongate shield 120 moved into an intermediate position between the proximal and distal positions. The force required to slide the elongate shield 120 is reduced while in intermediate positions, to enhance the feedback provided by the raised humps 205 when the elongate shield 120 reaches the proximal, distal, or locked positions.

Figure 9:
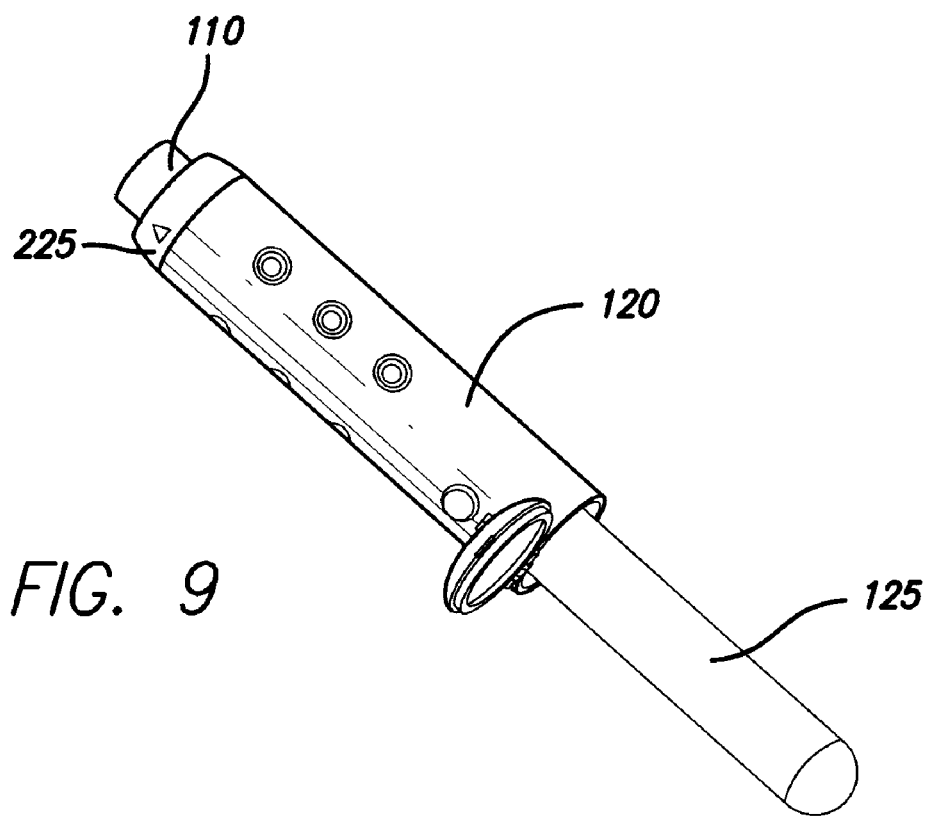
FIG. 9 is a perspective view of an embodiment of the present invention illustrating an elongate shield in a proximal position.

FIG. 9 illustrates the elongate shield 120 in the proximal position, exposing the heating body 125. The elongate shield 120 includes a shield taper 225, on the proximal end of the elongate shield 120.

Figure 10:
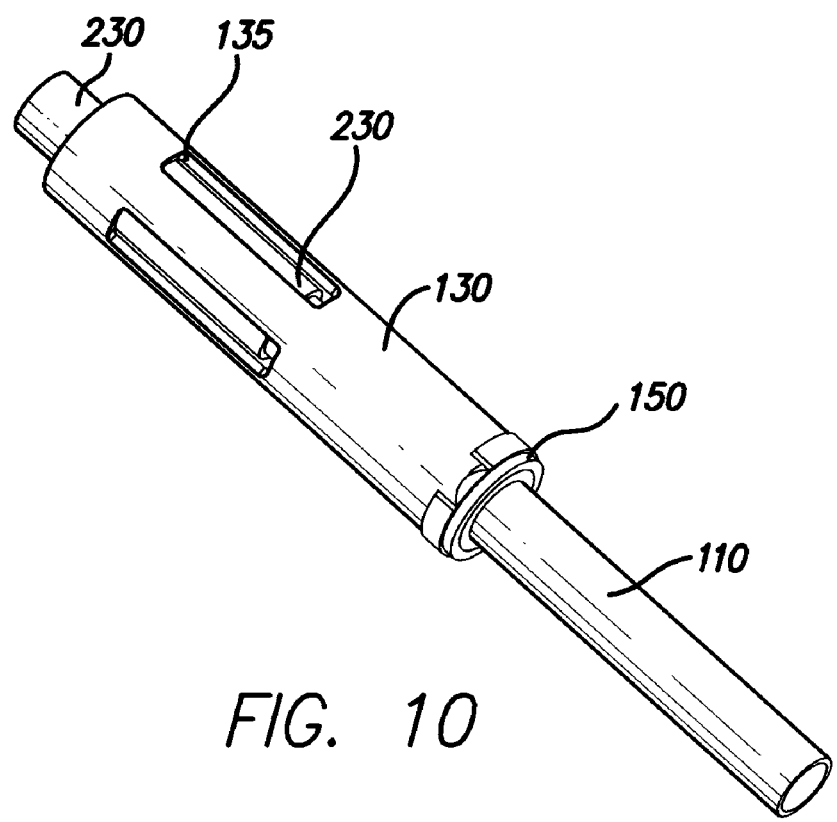
FIG. 10 is a perspective view of an embodiment of the present invention with a heating body removed to reveal an elongate inner body.

FIG. 10 illustrates the venting body 130, the heating body fastener 150, the elongate inner vessel 110, and a permeable sock 230. The heating body 125 is removed to expose the elongate inner vessel 110. The permeable sock 230 is positioned over the proximal end of the elongate inner vessel 110, visible on the proximal end of the elongate inner vessel 110 and visible through the body vents 135. In the illustrated embodiment, the permeable sock 230 extends in a distal direction along the elongate inner vessel 110, so as to be adjacent to the body vents 135.

The permeable sock 230 provides filtering of the airflow, by directly covering the proximal opening of the elongate inner vessel 110. Accordingly, the permeable sock 230 can catch and therefore minimize passage of any substances, such as tar or portions of the vaporizable substance, into the user's mouth or airway passages during use.

As illustrated, permeable sock 230 is flexible and elastically grips the proximal end of the elongate inner vessel 110. However, the permeable sock 230 can include a rigid support with filtration portions, structured to interface with the elongate outer vessel 105 and/or the elongate inner vessel 110 to support the filtration portions in the airflow pathway. Preferably, the permeable sock 230 is made of a material such as organic or untreated cotton, having a weight and needle knit corresponding to preferred filtration and humidification effects. Furthermore, the permeable sock 230 can include a pull-string, for selectively cinching the permeable sock 230 and tightening its grip on the elongate inner vessel 110.

The permeable sock 230 is positioned along the airflow pathway to provide a two-stage humidification effect, as well as to cool the resultant vapor to be inhaled, as well as also cooling the elongate inner vessel and airflow pathway. During use, the permeable sock 230 can be moistened, such that it retains the moisture and selectively releases the moisture into the airflow during use. The airflow passes along the outer surface of the moistened permeable sock 230, picking up moisture. Then, as the airflow exits the proximal end of the elongate inner vessel 110, it passes through the proximal end of the moistened permeable sock 230, again picking up moisture during the second stage of humidification.

Figure 11:
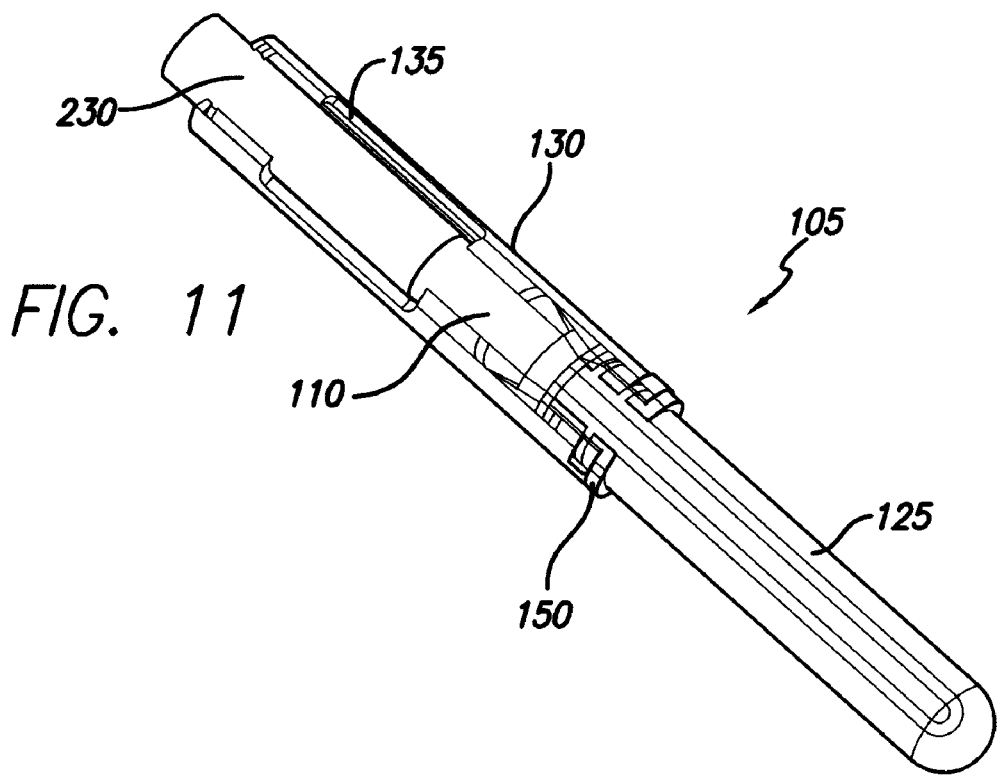
FIG. 11 is a partial cross-sectional view of the embodiment illustrated in FIG. 2 with a portion of the elongate outer vessel and fastener removed, illustrating the elongate inner vessel.

FIG. 11 illustrates the permeable sock 230 via a partial cut-away view of the elongate outer vessel 105. The permeable sock 230 is arranged on the end of the elongate inner vessel 110. The elongate inner vessel 110 extends within the venting body 130, heating body fastener 150, and the heating body 125. As illustrated, the permeable sock extends distally beneath the majority of the body vents 135. However, it is possible to adjust the length of the permeable sock 230 and/or the body vents 135, to affect the humidification effect, the ability of the airflow to pass through the vents, and the extent of overlap between the body vent openings and the permeable sock extension along the elongate inner vessel.

Figure 12:
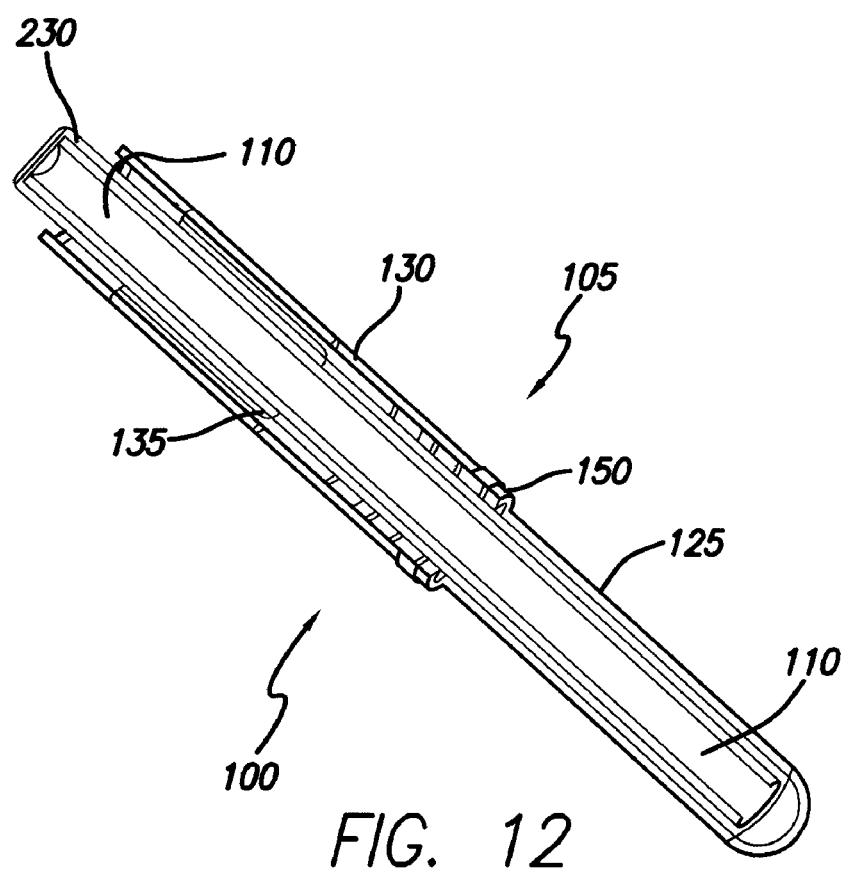
FIG. 12 is a perspective cross-sectional view of the embodiment illustrated in FIG. 2 along line A-A.

FIG. 12 illustrates a cross section of the portable vaporizer 100 showing an airflow pathway including the spacing between elongate outer 105 and inner 110 vessels. During use, the airflow pathway flows along the body vents 135, the space between the venting body 130 and the permeable sock 230, along the space between the elongate inner vessel 110 and the venting body 130, along the space between the heating body 125 and the elongate inner vessel 110, through the distal end of the elongate inner vessel 110, through an inner passage of the elongate inner vessel 110, and out the proximal end of the elongate inner vessel 110 through the proximal end of the permeable sock 230. Preferably, the airflow pathway includes a specific flow pattern that prevents substantially wasteful eddy current, to provide predictable results during heating and use by maintaining the proper temperatures.

Figure 13:
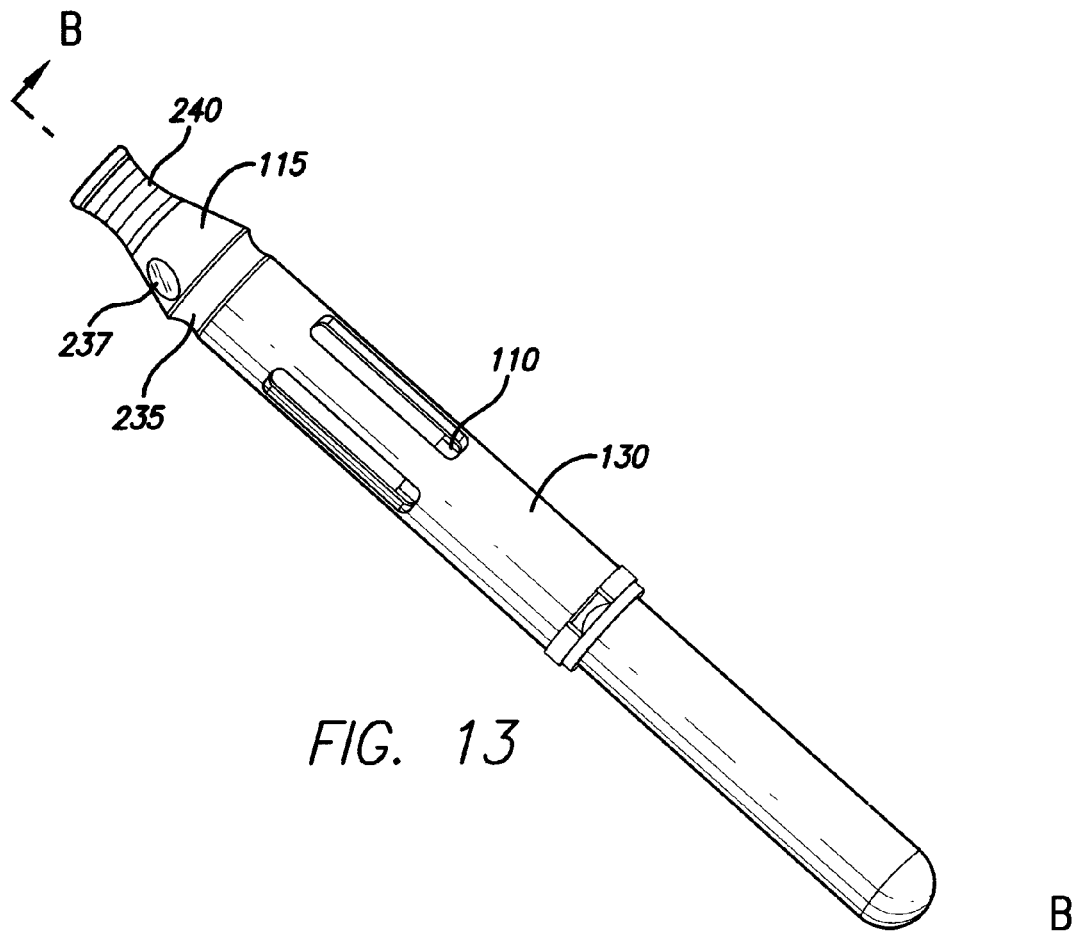
FIG. 13 is a perspective view of an embodiment of the present invention illustrating a mouthpiece.

FIG. 13 illustrates mouthpiece 115 connected to the proximal end of the elongate inner vessel 110 and the proximal end of the venting body 130. The mouthpiece 115 includes an indented ring 235, which can provide a gripping surface for the user. The mouthpiece 115 can also include an in-molded rubber grip 237. The mouthpiece also includes bite ring 240. Preferably, the bite ring 240 is constructed from a flexible material for cushioning, for elastic retention on the mouthpiece 115, and for removal to facilitate replacement or cleaning. Alternatively, the bite ring 240 can be in-molded to the mouthpiece 115.

Figure 14:
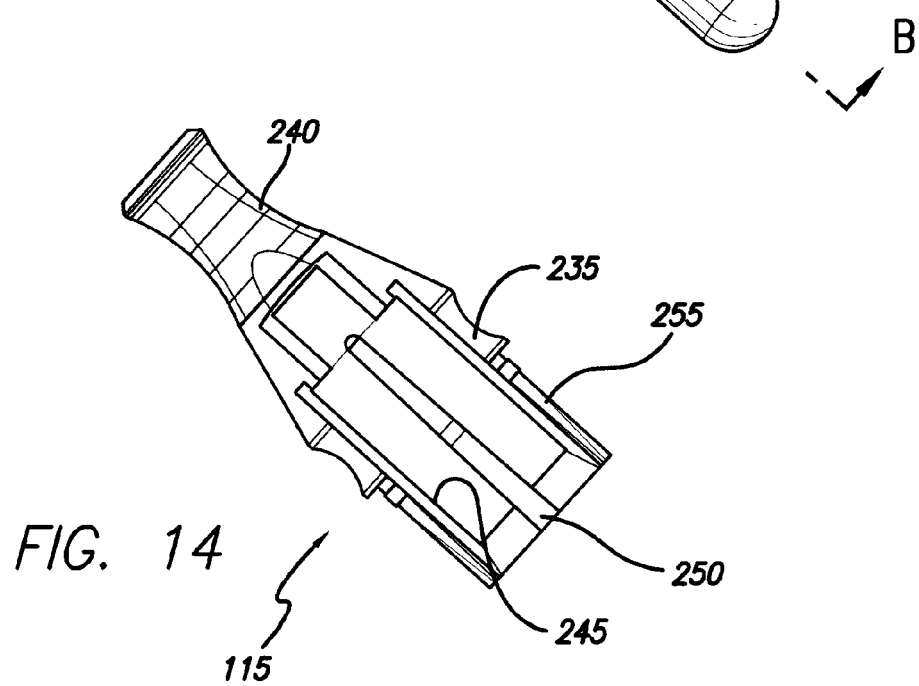
FIG. 14 is a longitudinal cross-sectional view of the mouthpiece illustrated in FIG. 13 taken along line B-B.

FIG. 14 illustrates a cross-sectional view of the mouthpiece 115 in greater detail. The mouthpiece 115 includes a mouthpiece inner grip 245, configured to grip the proximal end of the elongate inner vessel. The mouthpiece inner grip 245 extends inward to grip the elongate inner vessel. The mouthpiece inner grip 245 includes a varying inward extension to accommodate variations in the elongate inner vessel. As illustrated, the mouthpiece inner grip 245 includes larger and smaller inwardly extending portions. For example, if the permeable sock is installed on the elongate inner vessel, the mouthpiece inner grip 245 will grip the permeable sock along the larger inwardly extending portion of the mouthpiece inner grip 245. If the elongate inner vessel is used without the permeable sock, the mouthpiece inner grip 245 will grip the elongate inner vessel along the smaller inwardly extending portion of the mouthpiece inner grip 245.

The mouthpiece 115 includes one or more mouthpiece channels 250 along the inner surface of the mouthpiece inner grip 245. The mouthpiece channels 250 provide a moisture pathway for communicating moisture from the distal portions of the permeable sock 230 to the proximal end of the permeable sock 230. Accordingly, moisture is distributed between the proximal end and distal portions of the permeable sock 230. Moisture distribution enhances the two-stage humidification effect, as well as the cooling of the elongate inner vessel and airflow pathway.

The mouthpiece 115 includes a mouthpiece outer grip 255. The mouthpiece outer grip 255 is configured to grip the inner surface of the proximal end of the venting body 130. Accordingly the mouthpiece 115 can simultaneously grip the elongate inner vessel 110 and the venting body 130, thereby providing additional stabilization and protection of the inner vessel 110. Furthermore, the mouthpiece 115 is arranged in an aesthetically pleasing and convenient orientation to maintain the lines of the elongate outer vessel 105. Accordingly, when the elongate shield 120 is in the proximal position, a proximal end of the elongate shield 120 covers the indented ring 235 of the mouthpiece 115. The shield taper 225 preferably corresponds to a taper of the mouthpiece 115, such that the mouthpiece 115 extends the shield taper 225 in an aesthetically pleasing and convenient alignment.

Figure 15:
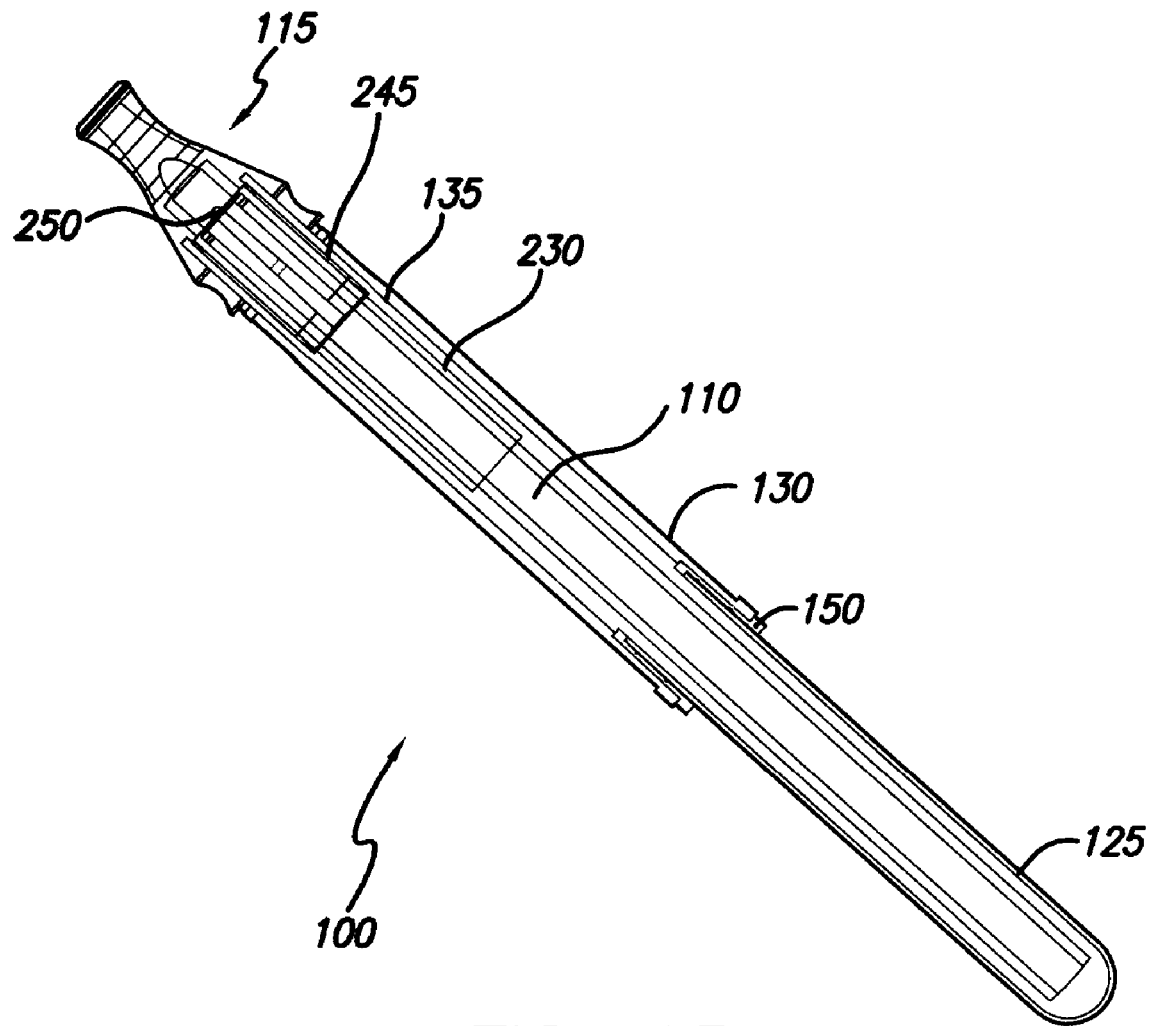
FIG. 15 is a longitudinal cross-sectional view of the embodiment illustrated in FIG. 13 taken along line B-B.

FIG. 15 illustrates a cross-sectional view of the portable vaporizer 100 with the mouthpiece 115 installed and the elongate shield 120 removed. The mouthpiece inner grip 245 is gripping the proximal end of elongate inner vessel 110 via the permeable sock 230. A portion of one of the mouthpiece channels 250 is visible, illustrating the moisture pathway to the proximal end of the permeable sock 230.

Figure 16:
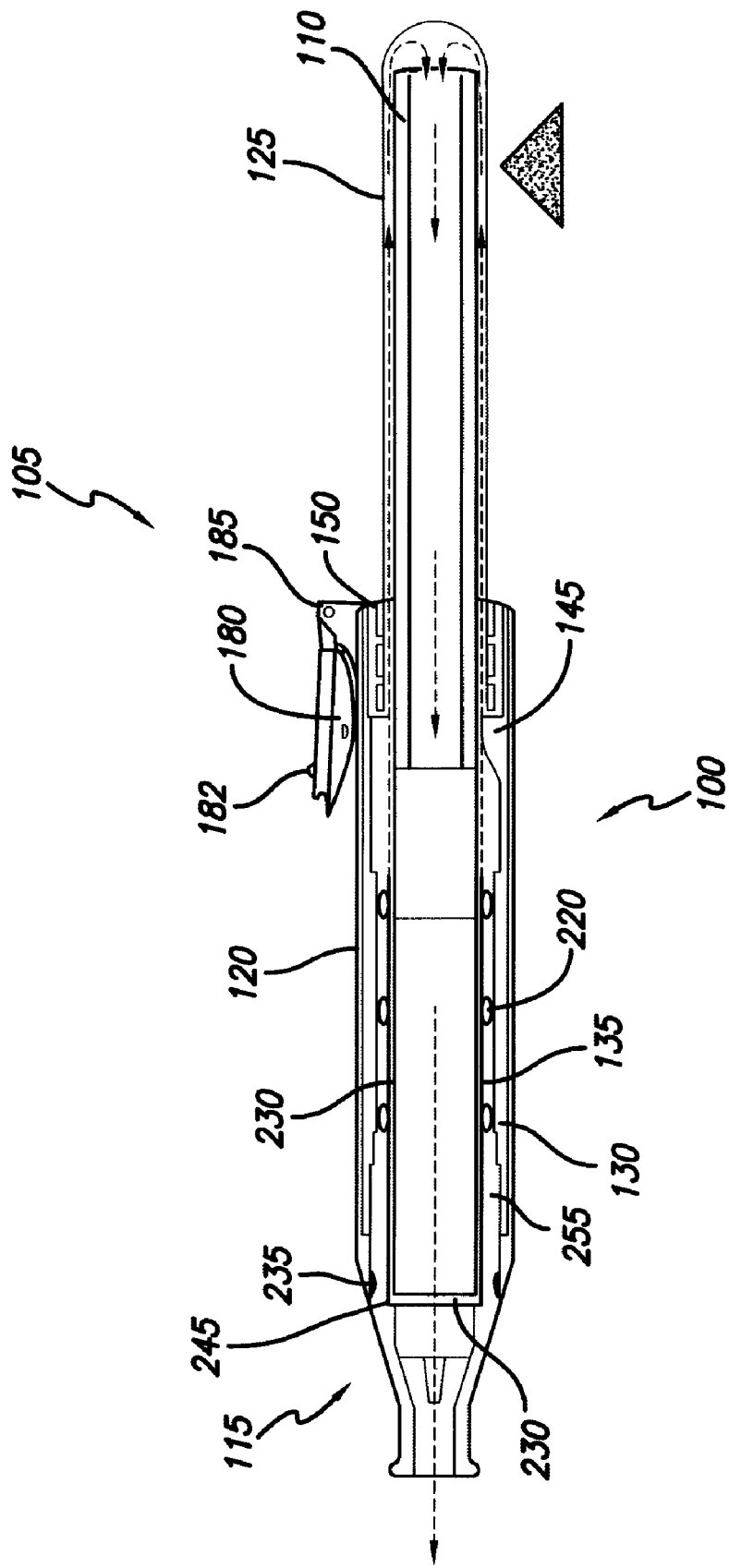
FIG. 16 is a longitudinal cross-sectional view of an embodiment of the present invention illustrating an end cap and airflow pathway.

FIG. 16 illustrates a cross-section of the portable vaporizer 100 configured for use. The airflow pathway includes the shield vents 220 of the elongate shield 120, because the elongate shield 120 is arranged in the proximal position that orients the shield vents 220 over the body vents 135. The heating body 125 is exposed for heating, and the end cap 180 is secured in the open position. End cap 180 includes cap feet 182, which allow the end cap 180 to serve as a stand. The cap feet 182 can support the portable vaporizer 100 while the end cap 180 is in the secured open position and the portable vaporizer is placed with the end cap 180 facing the ground.

In the illustrated embodiment, the inner vessel 110 is stabilized by the stabilizers 145 of the venting body 130, and the mouthpiece inner grip 245 of the mouthpiece 115. The heating body 125 is fastened to the venting body 130 via the heating body fastener 150.

Figure 17:
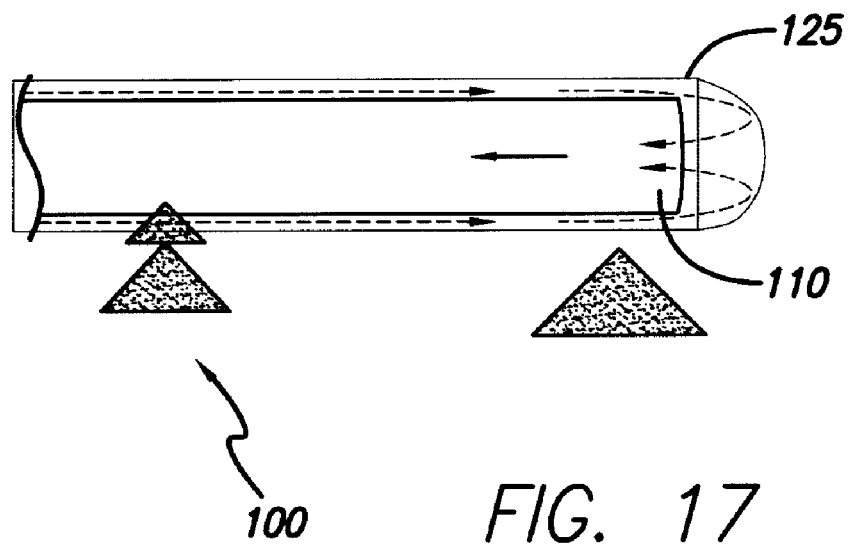
FIG. 17 is a detailed cross-sectional view of a portion of the airflow pathway of FIG. 16.

FIG. 17 illustrates heating of the portable vaporizer 100. Heat is applied to the heating vessel 125, which transfers the heat to the airflow and the inner passage of the inner vessel 110. Due to the composition and arrangement of the heating body 125 and the inner vessel 110, heat can be applied directly/radiantly to the inner passage of the inner vessel 110.

Figure 18:
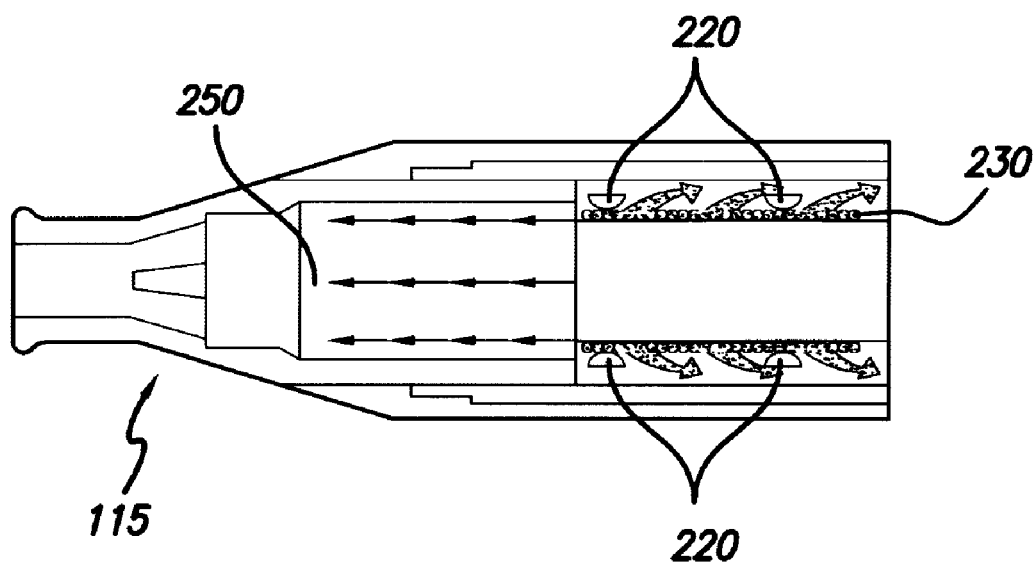
FIG. 18 is a detailed cross-sectional view of a portion of the moisture pathway of FIG. 16.

FIG. 18 illustrates the moisture pathway provided by the mouthpiece channels 250 of the mouthpiece 115, and the two-stage humidification effect. Capillary action and suction (provided by puffing on the mouthpiece) cause moisture to move along the moisture pathway from the distal end to the proximal end of the permeable sock 230 where the airflow passes through the proximal end of the permeable sock 230. Additionally, the moisture enters the airflow pathway at the beginning of the airflow pathway, as the airflow passes along the permeable sock 230 after entering the shield vents 220.

The illustrated embodiment of FIG. 17 arranges the elongate inner vessel 110 such that its distal end and the inside surface of the distal end of the heating body 125 do not make contact with one another at all, there being a space between them when assembled. The distance between the distal end of the elongate inner vessel 110 and the inner surface of the distal end of the heating body 125 can be arranged according to the heating requirements of the substance. Alternatively, the distance can be small enough such that particles of the vaporizable substance are confined by the inner surface of the heating body 125 within the open distal end of the inner vessel 110, preventing them from moving out into the space between the inner and outer vessel and out of optimal vaporizing position, when the device is jostled.

Alternatively, air inlet openings can be made in the surface of the elongate inner vessel 110 near the distal end so as to allow air to pass from the space between the elongate inner vessel 110 and the heating body 125 through the air inlet openings into the vaporization chamber containing the substance at the distal end of the inner vessel 110. Another embodiment is a combination of a gap/gaps at the abutment area between the distal end of the elongate inner vessel 110 and distal end of the heating body 125, and air inlet openings through the surface of the vaporization chamber of the elongate inner vessel 110.

Figure 19:
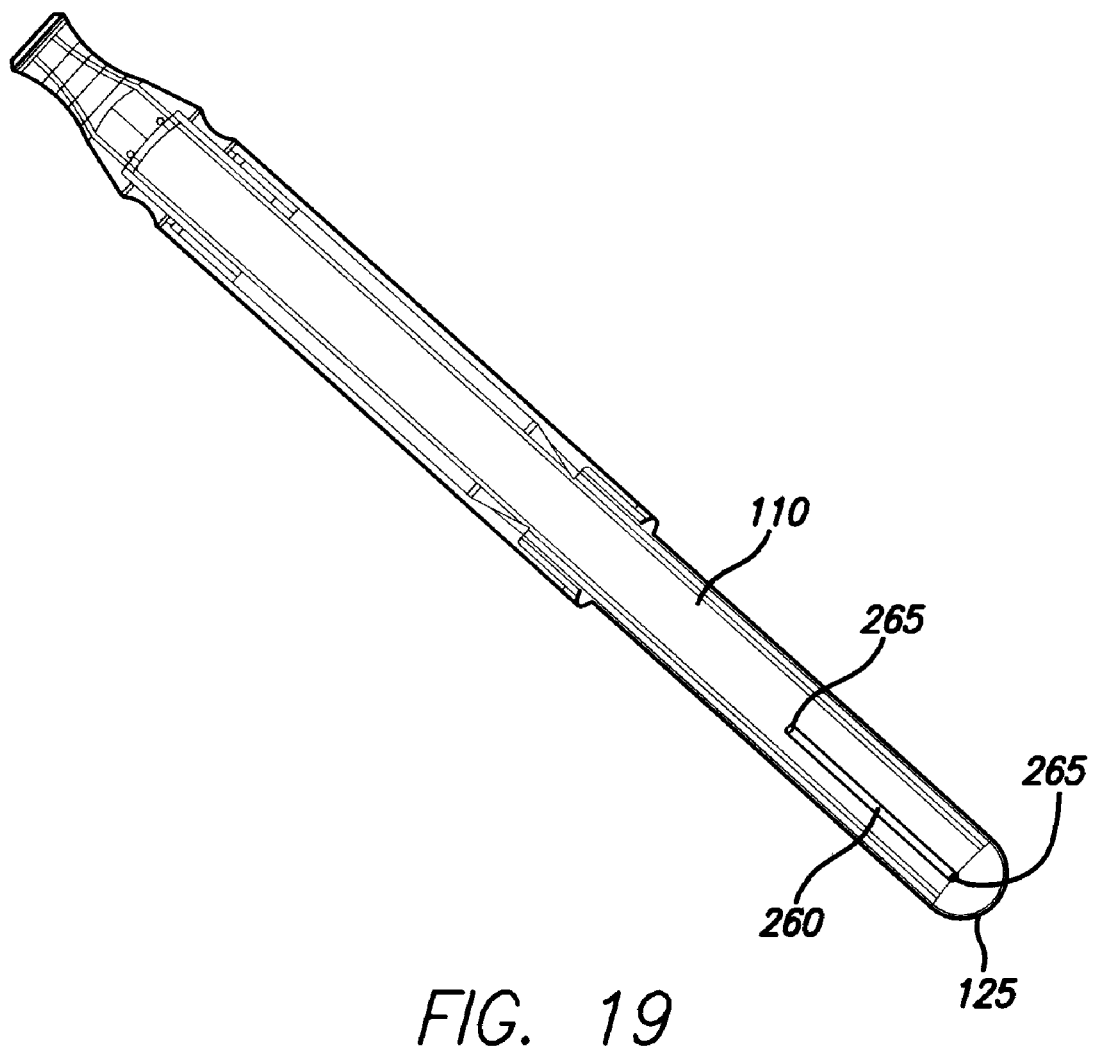
FIG. 19 is a longitudinal cross-sectional view of the embodiment illustrated in FIG. 13 taken along line B-B, illustrating a retainer.

FIG. 19 illustrates a linear retainer 260. The linear retainer 260 is structured to retain the substance at the distal end of the inner passage of the elongate inner vessel 110, through use of one or more linear retainer clips 265. The linear retainer 260 illustrated in FIG. 19 includes two linear retainer clips 265, connected symmetrically with respect to each other. Accordingly, the linear retainer 260 can be positioned with either end facing toward the distal end of the elongate inner vessel 110. One of the linear retainer clips 265 grips the distal end of the elongate inner vessel 110, and the other retainer clip 265 is positioned to extend proximally into the inner passage, to grip the substance positioned within the inner passage and to prevent the substance from being carried by the airflow within the inner passage in a proximal direction.

The linear retainer 260 is well-suited to retain substances that have a monolithic structure, such as pre-packaged cigarettes. One of the linear retainer clips 265 can be inserted into a portion of the substance, thereby fixing the substance to the linear retainer 260. A portion of the linear retainer 260 can be marked with indicia, enabling an end of the substance to be aligned with the linear retainer 260 for optimal positioning with respect to the distal end of the inner vessel 110. For example, the linear retainer 260 can include a scribe line indicating where the substance should be positioned in relation to the linear retainer 260, when the retainer clip 265 is pierced into the side of the substance, to align the end of the substance with the scribe line. Accordingly, when the assembly of the substance (e.g., cigarette) and linear retainer 260 are inserted into the distal end of the inner vessel 110, the cigarette is positioned at a specific distance from the distal end of the inner vessel 110 and heating body 125.

Figure 20:
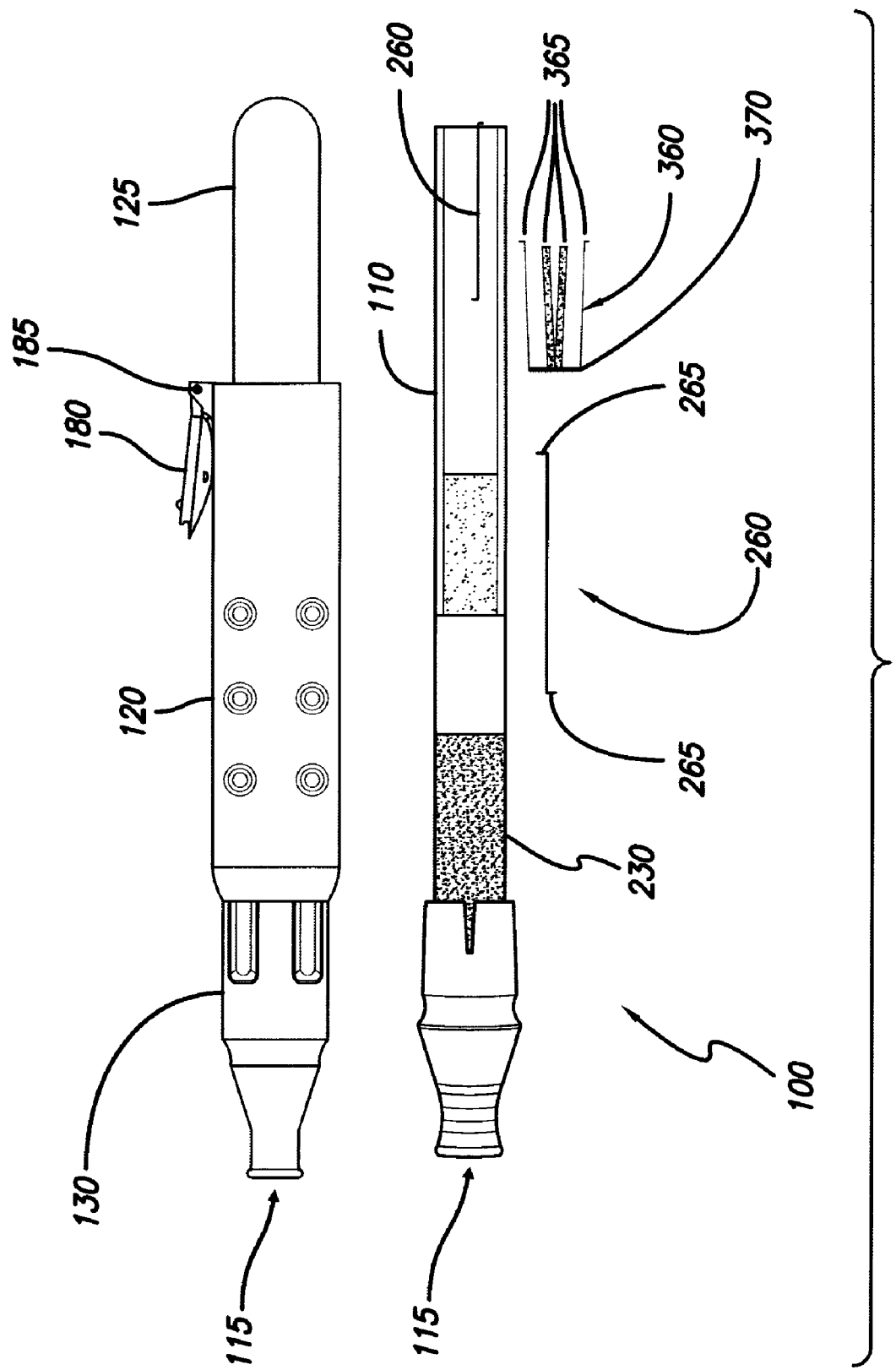
FIG. 20 is an exploded view of an embodiment of the present invention illustrating a linear retainer and a compound retainer.

FIG. 20 illustrates a partially exploded view of the portable vaporizer 100, including linear retainer 260 having linear retainer clips 265, and compound retainer 360 having compound retainer clips 365. Compound retainer 360, as illustrated, includes four compound retainer clips 365, arranged radially to grip the distal end of the elongate inner vessel 110. Preferably, the compound retainer clips 365 are configured to diverge slightly along a proximal-distal direction, providing the compound retainer 360 a spring-loaded grip along the inner passage of the elongate inner vessel 110.

Compound retainer 360 includes a compound retainer screen 370, structured to have an outer diameter corresponding to the inner diameter of the inner vessel 110. Accordingly, the compound retainer screen 370 screens the substance and prevents particles of the substance from traveling along the airflow pathway. Compound retainer screen 370 is well-suited for use with non-monolithic substances, including loose tobacco, herbs, or other combustible plant substances. Because the compound retainer screen 370 readily transmits the airflow pathway, the user can conveniently load the non-monolithic substance into the inner vessel against the compound retainer screen 370 by providing a suction on the proximal end of the elongate inner vessel 110, which is transmitted to the distal end that suctions the substance into the inner vessel 110 against the compound retainer screen 370. Alternatively, the user can manually pack the substance into the assembly of the inner vessel 110 and retainer.

The compound retainer 360 may be configured to have different lengths, allowing it to extend to different lengths from the distal end of the elongate inner vessel 110. Accordingly, the substance can be retained at different positions, and/or a larger or smaller amount of the substance can be accommodated within the elongate inner vessel 110, as desired. Further, the pattern and/or shape of screening holes of the compound retainer screen 370 can be varied in numerous ways without problem. For example, the screening holes could be round, slotted, diamond-shaped or any other shapes. There are many types of screening hole patterns that could effectively function as a screening mechanism to allow vapors to pass and prevent solid unvaporized substances from continuing past the compound retainer 360 along the airflow pathway. The number, shape and size of screening holes selected will affect the drawing pressure necessary to produce a given airflow through the device. Furthermore, the number and configuration of the linear retainer clips 265 and compound retainer clips 365 can be varied to accommodate various vaporizable substances or ease of construction and airflow. Preferably the retainer, retainer clips, and screen are made of a non-reactive material, such as stainless steel that has been electrically charge passified and "true sintered," to prevent metallic separation, to minimize reactions with the airflow and/or substance, and to fuse the screen together. The retainers can be assembled using spot welding.

The retainer clips can be configured to prevent the distal end of the inner vessel 110 from contacting the distal end of the heating body 125. In such a configuration, the linear and/or compound retainer clips have a thickness, extending distally from the end of the elongate inner vessel 110, corresponding to the minimum gap desired between the ends of the elongate inner vessel 110 and heating body 125. Accordingly, when the elongate inner vessel 110 is moved towards the distal end of the heating body 125, the retainer clips will contact both surfaces and maintain a minimum spacing between the ends of the elongate inner vessel and heating body. Multiple retainer clips can be used simultaneously. For example, a retainer clip can be arranged on the proximal end of the substance, and a second retainer clip can be arranged on the distal end of the substance, thereby sealing in the substance within the elongate inner vessel 110.

Figure 21:
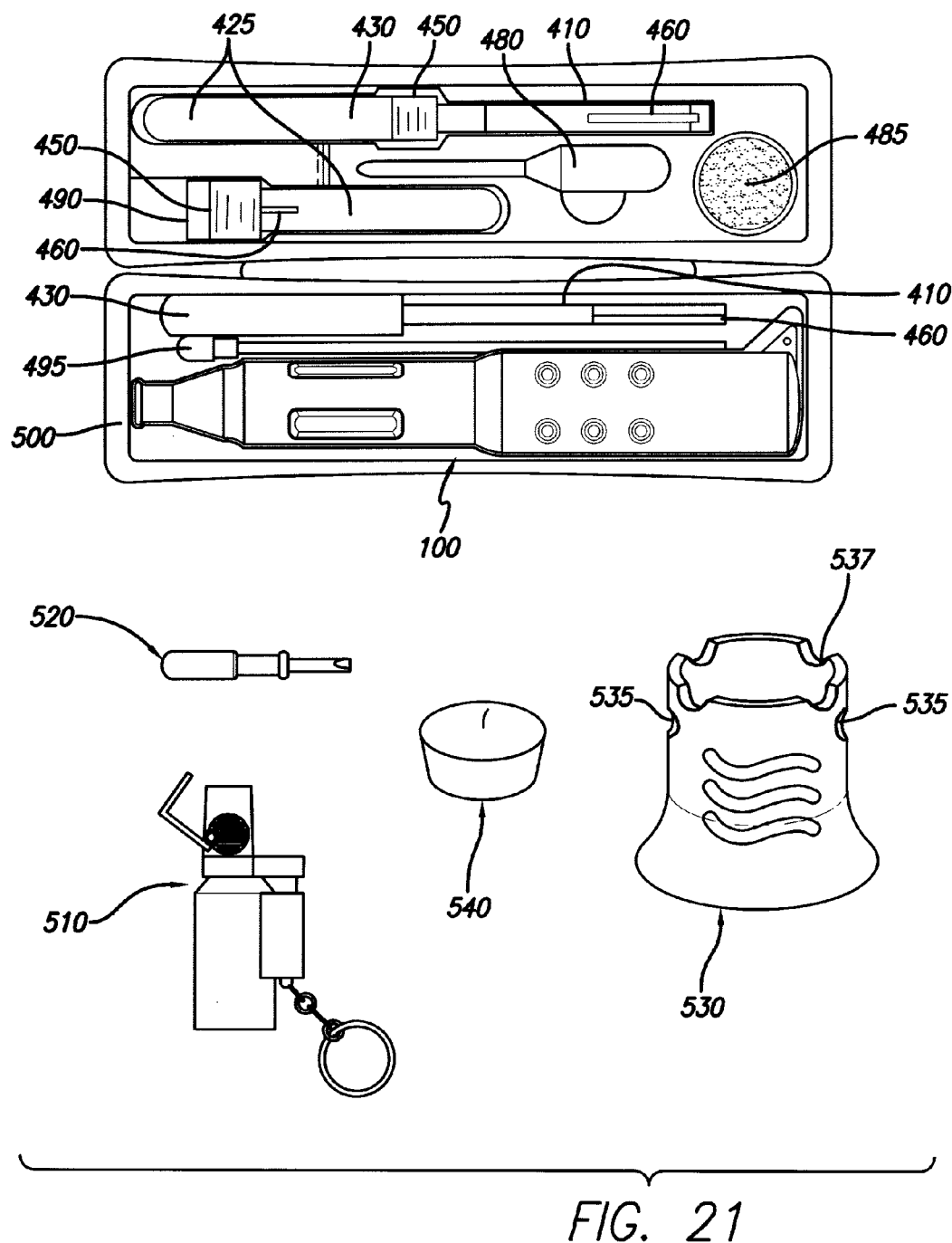
FIG. 21 is a longitudinal view of an embodiment of the present invention illustrating a kit.

FIG. 21 illustrates a portable vaporizer kit, including extra supplies such as extra heating bodies 425, extra permeable socks 430 stored within the extra heating bodies 425, extra heating body fasteners 450, extra retainers 460, extra elongate inner vessels 410, and stored substances. The vaporizer kit additionally includes a water pipette 480 for moisturizing the permeable sock, a humidor disc 485 for humidifying the contents of the vaporizer kit, foam stoppers 490 for containing stored substances within the extra heating bodies and enabling the humidification effect within the extra heating bodies and stored substances, a cleaning swab 495 for both cleaning and packing the substance in the portable vaporizer, a portable storage case 500, a portable heat source 510, and a tool 520 for aiding assembly/disassembly of the portable vaporizer and for adjusting the portable heat source. Accordingly, the portable vaporizer kit enables a user to conveniently store and carry all necessary equipment for using the portable vaporizer. The vaporizer kit can additionally include cleaning supplies, such as disposable wipes and a safety wipe. Preferably, the safety wipe is constructed from a material that can provide a cleaning function, and that is thick enough such that it can be used to protect the user's hands from high temperatures. Furthermore, the wipe can be thick enough to protect the user's hands from broken glass, from either the heating body or the elongate inner vessel. Preferable safety wipe materials include leather, Kevlar®, canvas, and other heavy fabrics.

The kit can also include a support stand 530 configured to accept candles 540 as a heat source. The support stand includes cut-out holes 535 to position the assembled portable vaporizer such that the heating body is positioned above a candle's flame, such that the portable vaporizer can be rotated to provide a rotisserie heating effect. After use, when the candle's flame is extinguished, upper indentions 537 provide a support for the disassembled elongate inner vessel 110, allowing the elongate inner vessel 110 and moistened permeable sock 230 to air dry.

Operation of the Portable Vaporizer

In order to use the portable vaporizer 100, one can load the distal end of the elongate inner vessel 110 with vaporizable substance. To accomplish this, the elongate inner vessel 110 and elongate outer vessel 105 are disassembled from one another. Non-monolithic vaporizable substances should be formed of small enough particles to maximize surface area but of sufficient particle size so as to minimize escape of the particles into the airflow beyond the retainer 260 or 360. A suitable grinding device may be employed to produce appropriately sized particles, if desired.

The user may directly insert by hand the vaporizable substance into the elongate inner vessel 110, or the user can apply suction to the proximal end of the elongate inner vessel 110 to suck the vaporizable substance into the distal end of the elongate inner vessel 110 against the retainer 260 or 360. A second retainer can be loaded to the distal end of the elongate inner vessel 110, to prevent the substance from falling out of the open distal end of the elongate inner vessel 110.

After the substance has been loaded, the mouthpiece 115 is positioned on the proximal end of the elongate inner vessel 110, which is slid fully into the elongate outer vessel 105 so that the mouthpiece outer grip 255 grips the inner surface of the proximal end of the elongate outer vessel 105.

Assembly of the portable vaporizer 100 is facilitated by a snap-together construction, such that all parts frictionally engage each other without a need for separate tools or adhesives. Alternatively, the construction can be facilitated by screw-together or other interaction between the various parts of the portable vaporizer 100.

As an alternative to loading a substance within the elongate inner vessel 110, or additionally, vaporizable essential oils can be applied to the permeable sock 230. Oils can be applied directly to the permeable sock 230 while assembled, or they can be applied to the sock while removed from the elongate inner vessel 110. Accordingly, the portable vaporizer 100 can be used as an inhaler without the need to heat a substance within the heating body 125. The essential oils can furthermore be utilized in conjunction with a vaporizable substance heated within the heating body 125, to enhance the flavor of the vaporized substance.

During heating, the portable vaporizer 100 can be held substantially horizontal or tilted, so long as the user's hand, face, hair, or other sensitive parts are not exposed to dangerous levels of heat from the heat source. To avoid obstructing the airflow pathway through the portable vaporizer 100, when holding the assembly during use, the body vents 135 or shield vents 220 should not be obstructed. The user can hold the device by the elongate shield 120, without obstructing shield vents 220, while the elongate shield 120 is in the proximal position.

To begin vaporization, a heat source, such as a flame from an ordinary cigarette lighter or hand-held portable torch, is held under the heating body 125 such that the tip of the flame preferably is just touching the heating body 125 along its most distal 1-2 cm in length. This heating area is preferred for most heating applications. However, applying heat more proximally, provides successful functioning of the device, and may even be preferred in some instances.

The user inhales through the mouthpiece 115 at the proximal end of the elongate inner vessel 110. As air is inhaled through the mouthpiece 115, air is drawn into the portable vaporizer 100 through the airflow pathway, passing through shield vents 220, body vents 135, along the permeable sock 230 and the space between adjacent inner and outer surfaces of the elongate inner 110 and outer 105 vessels, distally between the distal end of the elongate inner vessel 110 and the inner surface of the closed distal end of the heating body 125, then through the vaporizable substance retained in the elongate inner vessel 110 by the retainer 260/retainer 360, then proximally through the permeable sock 230, through the mouthpiece 115 and finally, into the user's mouth and lungs.

The flame heats the glass of the heating body 125, which in turn heats the air passing between the elongate inner 110 and outer 105 vessels in the heating body 125. If the permeable sock 230 has been moistened, the airflow will include moisture due to the first-stage humidification effect of passing by the permeable sock 230. The permeable sock 230 can be pre-moistened, and/or moistened during use via the body vents 135 or the mouthpiece 115. The heated air then travels through the vaporizable substance, heating the vaporizable substance. This is the primary heating mechanism, which isolates the substance from the heated glass of the heating body 125 within the inner vessel, spaced from the heating body 125 and surrounded by an envelope of airflow pathway. Secondarily, the heated glass of the heating body 125 heats the air within the heating body, which in turn heats the glass of the elongate inner vessel 110 that subsequently conducts heat to the vaporizable substance in the elongate inner vessel 110. The vaporizable substance is thus heated to a suitable temperature to cause the release of desired volatile constituents, which are carried by the airflow through the permeable sock 230 which provides filtration and a second-stage humidification effect.

When substance-containing portions of the heating body 125 and elongate inner vessel 110 are partially or fully transparent, it is possible to visually monitor the substance while it is being heated and undergoing vaporization. Accordingly, the user can adjust the airflow and heat source to provide pinpoint heating to the substance, and to prevent improper heating. Furthermore, the user can visually determine when the substance is fully vaporized.

Moisture preferably can be applied to the permeable sock 230 before and during use, in order to provide a pleasing humidification effect and to cool the airflow drawn out of the portable vaporizer 100. The shield vents 220 and body vents 135 are arranged such that moisture can be applied directly to the permeable sock 230 through the vents, without needing to disassemble the portable vaporizer 100. Moisture can also be applied to the proximal end of the permeable sock 230 directly through the mouthpiece 115.

Visual and physical (e.g., airflow temperature) feedback enable the user to operate the vaporizer most effectively. When the air coming through the mouthpiece 115 starts to feel warm, vaporization is beginning. If there is any burnt taste at all, or if smoke rather than a vapor mist is produced, then the flame is being applied too intensely and should be removed momentarily. Once the unit is up to vaporizing temperature, the lighter may be removed and the unit will stay hot enough to continue vaporizing substance such that another effective inhalation may still be made. Continue heating and inhaling until all desired volatiles are released from the substance in the portable vaporizer 100. Changes in color, taste, etc. will be indicators as to whether there is any more to be gained from continued heating of the current substance in the portable vaporizer 100. When the substance is used as much as desired, disassemble the unit being careful not to touch the hot distal ends of the heating body 125 and elongate inner vessel 110. Remove the mouthpiece 115, thereby removing the elongate inner vessel 110 from the elongate outer vessel 105. Empty the elongate inner vessel 110 by dumping out or by blowing through the mouthpiece, and then refill for the next usage.

If any black soot gathers on the outside of the heating body 125 due to use of a soot producing heat source (e.g., disposable lighter or candle), the soot may be wiped away using disposable wipes or a safety cloth. Use of a refillable butane jet lighter will not produce such soot and is therefore preferred.

What is claimed is:

1. A device for vaporizing volatile constituents of a substance the device comprising:
   an elongate outer vessel having an inner surface, an outer surface, a proximal end and a closed distal end, said closed distal end formed by a heating body comprising a material that can withstand heat required to vaporize said volatile constituents, said proximal end formed by a venting body;
   an elongate inner vessel having an inner passage dimensioned to receive the substance an outer surface and open distal and proximal ends and being insertable into said elongate outer vessel and extending within the heating body and the venting body so as to leave a space between adjacent walls of said elongate inner vessel and said heating and venting bodies, and a space between the inner vessel open distal end and the outer vessel closed distal end;
   one or more body vents located on the venting body away from the heating body for admitting atmospheric air along an airflow pathway formed by the space between the inner surface of the elongate outer vessel and the outer surface of the elongate inner vessel, the space between the distal ends of the elongate inner and outer vessels the inner passage, and the proximal end of the elongate inner vessel;
   wherein the elongate outer vessel further comprises an elongate shield configured to protect the heating body and prevent inadvertent contact with the heating body; and
   wherein the elongate shield further comprises one or more shield vents.

2. A device for vaporizing volatile constituents of a substance, the device comprising:
   an elongate outer vessel having an inner surface, an outer surface, a proximal end and a closed distal end, said closed distal end formed by a heating body comprising a material that can withstand heat required to vaporize said volatile constituents, said proximal end formed by a venting body;
   an elongate inner vessel having an inner passage dimensioned to receive the substance, an outer surface and open distal and proximal ends and being insertable into said elongate outer vessel and extending within the heating body and the venting body so as to leave a space between adjacent walls of said elongate inner vessel and said heating and venting bodies, and a space between the inner vessel open distal end and the outer vessel closed distal end;
   one or more body vents located on the venting body away from the heating body for admitting atmospheric air along an airflow pathway formed by the space between the inner surface of the elongate outer vessel and the outer surface of the elongate inner vessel, the space between the distal ends of the elongate inner and outer vessels the inner passage, and the proximal end of the elongate inner vessel;
   wherein the elongate outer vessel further comprises an elongate shield configured to protect the heating body and prevent inadvertent contact with the heating body; and
   wherein the elongate shield is slidable between a distal position and a proximal position.

3. The device of claim 2, wherein the elongate shield is rotatable about the outer vessel and rotatably clicks into a locked distal position by rotating the elongate shield from the distal position to the locked distal position, such that the locked distal position is associated with a retentive increase in rotational resistance.

4. The device of claim 2, wherein the elongate shield is shaped to include a shield taper corresponding to an outer vessel taper such that when in the proximal position, the shield taper extends along the outer vessel taper.

5. The device of claim 2, wherein the elongate shield includes an end cap.

6. The device of claim 5, wherein the end cap includes a cap vent corresponding to a raised button on the elongate shield such that the end cap in an open position can be releasably secured to the elongate shield.

7. A device for vaporizing volatile constituents of a substance the device comprising:

an elongate outer vessel having an inner surface, an outer surface, a proximal end and a closed distal end, said closed distal end formed by a heating body comprising a material that can withstand heat required to vaporize said volatile constituents, said proximal end formed by a venting body;

an elongate inner vessel having an inner passage dimensioned to receive the substance an outer surface and open distal and proximal ends and being insertable into said elongate outer vessel and extending within the heating body and the venting body so as to leave a space between adjacent walls of said elongate inner vessel and said heating and venting bodies, and a space between the inner vessel open distal end and the outer vessel closed distal end;

one or more body vents located on the venting body away from the heating body for admitting atmospheric air along an airflow pathway formed by the space between the inner surface of the elongate outer vessel and the outer surface of the elongate inner vessel, the space between the distal ends of the elongate inner and outer vessels the inner passage, and the proximal end of the elongate inner vessel;

a mouthpiece removably attached to the proximal end of the inner vessel via an inwardly extending mouthpiece inner grip;

wherein inward extension of the mouthpiece inner grip varies along a proximal-distal direction to accommodate variations of the elongate inner vessel.

8. A device for vaporizing volatile constituents of a substance the device comprising:

an elongate outer vessel having an inner surface, an outer surface, a proximal end and a closed distal end, said closed distal end formed by a heating body comprising a material that can withstand heat required to vaporize said volatile constituents, said proximal end formed by a venting body;

an elongate inner vessel having an inner passage dimensioned to receive the substance an outer surface and open distal and proximal ends and being insertable into said elongate outer vessel and extending within the heating body and the venting body so as to leave a space between adjacent walls of said elongate inner vessel and said heating and venting bodies, and a space between the inner vessel open distal end and the outer vessel closed distal end;

one or more body vents located on the venting body away from the heating body for admitting atmospheric air along an airflow pathway formed by the space between the inner surface of the elongate outer vessel and the outer surface of the elongate inner vessel, the space between the distal ends of the elongate inner and outer vessels the inner passage, and the proximal end of the elongate inner vessel;

a mouthpiece removably attached to the proximal end of the inner vessel via an inwardly extending mouthpiece inner grip;

wherein the inner grip includes one or more mouthpiece channels to provide a moisture flow pathway along the outer surface of the elongate inner vessel.

9. A device for vaporizing volatile constituents of a substance, the device comprising an elongate outer vessel having an inner surface, an outer surface, a proximal end and a closed distal end, said closed distal end formed by a heating body comprising a material that can withstand heat required to vaporize said volatile constituents, said proximal end formed by a venting body;

an elongate inner vessel having an inner passage dimensioned to receive the substance an outer surface and open distal and proximal ends and being insertable into said elongate outer vessel and extending within the heating body and the venting body so as to leave a bodies, and a space between the inner vessel open distal end and the outer vessel closed distal end;

one or more body vents located on the venting body away from the heating body for admitting atmospheric air along an airflow pathway formed by the space between the inner surface of the elongate outer vessel and the outer surface of the elongate inner vessel, the space between the distal ends of the elongate inner and outer vessels the inner passage, and the proximal end of the elongate inner vessel;

a mouthpiece removably attached to the proximal end of the inner vessel via an inwardly extending mouthpiece inner grip;

wherein the mouthpiece is removably attached to the proximal end of the elongate outer vessel via a mouthpiece outer grip.

10. A device for vaporizing volatile constituents of a substance the device comprising:

an elongate outer vessel having an inner surface, an outer surface, a proximal end and a closed distal end, said closed distal end formed by a heating body comprising a material that can withstand heat required to vaporize said volatile constituents, said proximal end formed by a venting body;

an elongate inner vessel having an inner passage dimensioned to receive the substance an outer surface and open distal and proximal ends and being insertable into said elongate outer vessel and extending within the heating body and the venting body so as to leave a space between adjacent walls of said elongate inner vessel and said heating and venting bodies, and a space between the inner vessel open distal end and the outer vessel closed distal end;

one or more body vents located on the venting body away from the heating body for admitting atmospheric air along an airflow pathway formed by the space between the inner surface of the elongate outer vessel and the outer surface of the elongate inner vessel, the space between the distal ends of the elongate inner and outer vessels the inner passage, and the proximal end of the elongate inner vessel;

a retainer structured to retain the substance within the inner vessel;

wherein the retainer includes one or more clips structured to grip the distal end of the inner vessel.

* * * * *